(12) United States Patent
Martin et al.

(10) Patent No.: US 7,335,368 B2
(45) Date of Patent: Feb. 26, 2008

(54) **BVH-A2 AND BVH-A3 ANTIGENS OF GROUP B *STREPTOCOCCUS***

(75) Inventors: Denis Martin, St-Augustin-de-Desmaures (CA); Stephane Rioux, Beauport (CA); Martine Boyer, Ste-Foy (CA); Josée Hamel, Sillery (CA); Bernard R Brodeur, Sillery (CA)

(73) Assignee: ID Biomedical Corporation, Laval (CA)

( * ) Notice: Subject to any disclaimer, the term of this patent is extended or adjusted under 35 U.S.C. 154(b) by 565 days.

(21) Appl. No.: 10/398,570

(22) PCT Filed: Oct. 15, 2001

(86) PCT No.: PCT/CA01/01465

§ 371 (c)(1),
(2), (4) Date: Sep. 26, 2003

(87) PCT Pub. No.: WO02/31156

PCT Pub. Date: Apr. 18, 2002

(65) Prior Publication Data

US 2004/0071730 A1   Apr. 15, 2004

Related U.S. Application Data

(60) Provisional application No. 60/239,919, filed on Oct. 13, 2000.

(51) Int. Cl.
*A61K 39/09* (2006.01)

(52) U.S. Cl. .............. 424/244.1; 424/185.1; 424/190.1; 424/234.1; 424/192.1; 424/193.1; 530/300; 530/350; 435/975

(58) Field of Classification Search .......... 530/300, 530/350; 435/975; 424/185.1, 190.1, 234.1, 424/244.1, 192.1, 193.1
See application file for complete search history.

(56) References Cited

U.S. PATENT DOCUMENTS

| 6,342,223 B1 | 1/2002 | Michel et al. |
| 2003/0170782 A1 | 9/2003 | Le Page et al. |
| 2003/0228323 A1 | 12/2003 | Brodeur et al. |

FOREIGN PATENT DOCUMENTS

| WO | WO 9410317 | 5/1994 |
| WO | WO 9942588 | 8/1999 |
| WO | WO 0132882 | 5/2001 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Spellerberg et al., "LMB, a protein with similarities to the LRAI adhesin family, Mediates attachment to *Streptococcus agalactiae* to human laminin," American Society for Microbiology, Washington, US, Feb. 1999, pp. 871-878, vol. 67, No. 2, XP000973065, ISSN: 0019-9567, p. 871, left-hand column, last paragraph—right-hand column, paragraph 3, p. 877,P right-hand column, paragraph 2.
Jones A L et al., "Identification of *Streptococcus agalactiae* virulence genes in the neonatal rat sepsis model using signature-tagged mutagenesis," Molecular Microbiology, Blackwell Scientific, Oxford, GB, Sep. 2000, pp. 1444-1455, vol. 37, No. 6, XP001053730, ISSN: 0950-382X, abstract.

* cited by examiner

*Primary Examiner*—Jennifer E. Graser
(74) *Attorney, Agent, or Firm*—Seed IP Law Group PLLC

(57) ABSTRACT

Group B *streptococcus* polypeptides and polynucleotides encoding them are disclosed. Said polypeptides may be useful for the prophylaxis, diagnostic and/or therapy of streptococcal infection in mammals. Also disclosed are recombinant methods of producing the polypeptide antigens as well as diagnostic assays for detecting streptococcal infections, particularly GBS.

8 Claims, 6 Drawing Sheets

Figure 1 (SEQ ID NO: 1)

```
   1 ATGAGGGGAT CTCTCAGTAC TAAGCAATCT TACTCTCTAC GTAAATATAA ATTTGGTTTA
  61 GCATCAGTAA TTTTAGGGTC ATTCATAATG GTCACAAGTC CTGTTTTTGC GGATCAAACT
 121 ACATCGGTTC AAGTTAATAA TCAGACAGGC ACTAGTGTGG ATGCTAATAA TTCTTCCAAT
 181 GAGACAAGTG CGTCAAGTGT GATTACTTCC AATAATGATA GTGTTCAAGC GTCTGATAAA
 241 GTTGTAAATA GTCAAAATAC GGCAACAAAG GACATTACTA CTCCTTTAGT AGAGACAAAG
 301 CCAATGGTGG AAAAAACATT ACCTGAACAA GGGAATTATG TTTATAGCAA AGAAACCGAG
 361 GTGAAAAATA CACCTTCAAA ATCAGCCCCA GTAGCTTTCT ATGCAAAGAA AGGTGATAAA
 421 GTTTTCTATG ACCAAGTATT TAATAAAGAT AATGTGAAAT GGATTTCATA TAAGTCTTTT
 481 GGTGGCGTAC GTCGATACGC AGCTATTGAG TCACTAGATC CATCAGGAGG TTCAGAGACT
 541 AAAGCACCTA CTCCTGTAAC AAATTCAGGA AGCAATAATC AAGAGAAAAT AGCAACGCAA
 601 GGAAATTATA CATTTTCACA TAAAGTAGAA GTAAAAAATG AAGCTAAGGT AGCGAGTCCA
 661 ACTCAATTTA CATTGGACAA AGGAGACAGA ATTTTTTACG ACCAAATACT AACTATTGAA
 721 GGAAATCAGT GGTTATCTTA TAAATCATTC AATGGTGTTC GTCGTTTTGT TTTGCTAGGT
 781 AAAGCATCTT CAGTAGAAAA AACTGAAGAT AAAGAAAAAG TGTCTCCTCA ACCACAAGCC
 841 CGTATTACTA AAACTGGTAG ACTGACTATT TCTAACGAAA CAACTACAGG TTTTGATATT
 901 TTAATTACGA ATATTAAAGA TGATAACGGT ATCGCTGCTG TTAAGGTACC GGTTTGGACT
 961 GAACAAGGAG GGCAAGATGA TATTAAATGG TATACAGCTG TAACTACTGG GGATGGCAAC
1021 TACAAAGTAG CTGTATCATT TGCTGACCAT AAGAATGAGA AGGGTCTTTA TAATATTCAT
1081 TTATACTACC AAGAAGCTAG TGGGACACTT GTAGGTGTAA CAGGAACTAA AGTGACAGTA
1141 GCTGGAACTA ATTCTTCTCA AGAACCTATT GAAATGGTT TACCAAAGAC TGGTGTTTAT
1201 AATATTATCG GAAGTACTGA AGTAAAAAAT GAAGCTAAAA TATCAAGTCA GACCCAATTT
1261 ACTTTAGAAA AAGGTGACAA AATAAATTAT GATCAAGTAT TGACAGCAGA TGGTTACCAG
1321 TGGATTTCTT ACAAATCTTA TAGTGGTGTT CGTCGCTATA TTCCTGTGAA AAAGCTAACT
1381 ACAAGTAGTG AAAAAGCGAA AGATGAGGCG ACTAAACCGA CTAGTTATCC CAACTTACCT
1441 AAAACAGGTA CCTATACATT TACTAAAACT GTAGATGTGA AAAGTCAACC TAAAGTATCA
1501 AGTCCAGTGG AATTTAATTT TCAAAAGGGT GAAAAAATAC ATTATGATCA AGTGTTAGTA
1561 GTAGATGGTC ATCAGTGGAT TCATACAAG AGTTATTCCG GTATTCGTCG CTATATTGAA
1621 ATTTAA
```

Figure 2 (SEQ ID NO: 2)

```
   1 GATCAAACTA CATCGGTTCA AGTTAATAAT CAGACAGGCA CTAGTGTGGA TGCTAATAAT
  61 TCTTCCAATG AGACAAGTGC GTCAAGTGTG ATTACTTCCA ATAATGATAG TGTTCAAGCG
 121 TCTGATAAAG TTGTAAATAG TCAAAATACG GCAACAAAGG ACATTACTAC TCCTTTAGTA
 181 GAGACAAAGC CAATGGTGGA AAAAACATTA CCTGAACAAG GGAATTATGT TTATAGCAAA
 241 GAAACCGAGG TGAAAAATAC ACCTTCAAAA TCAGCCCCAG TAGCTTTCTA TGCAAAGAAA
 301 GGTGATAAAG TTTTCTATGA CCAAGTATTT AATAAAGATA ATGTGAAATG GATTTCATAT
 361 AAGTCTTTTG GTGGCGTACG TCGATACGCA GCTATTGAGT CACTAGATCC ATCAGGAGGT
 421 TCAGAGACTA AAGCACCTAC TCCTGTAACA AATTCAGGAA GCAATAATCA AGAGAAAATA
 481 GCAACGCAAG GAAATTATAC ATTTTCACAT AAAGTAGAAG TAAAAAATGA AGCTAAGGTA
 541 GCGAGTCCAA CTCAATTTAC ATTGGACAAA GGAGACAGAA TTTTTTACGA CCAAATACTA
 601 ACTATTGAAG GAAATCAGTG GTTATCTTAT AAATCATTCA ATGGTGTTCG TCGTTTTGTT
 661 TTGCTAGGTA AAGCATCTTC AGTAGAAAAA ACTGAAGATA AGAAAAAGT GTCTCCTCAA
 721 CCACAAGCCC GTATTACTAA AACTGGTAGA CTGACTATTT CTAACGAAAC AACTACAGGT
 781 TTTGATATTT TAATTACGAA TATTAAAGAT GATAACGGTA TCGCTGCTGT TAAGGTACCG
 841 GTTTGGACTG AACAAGGAGG GCAAGATGAT ATTAAATGGT ATACAGCTGT AACTACTGGG
 901 GATGGCAACT ACAAAGTAGC TGTATCATTT GCTGACCATA AGAATGAGAA GGGTCTTTAT
 961 AATATTCATT TATACTACCA AGAAGCTAGT GGGACACTTG TAGGTGTAAC AGGAACTAAA
1021 GTGACAGTAG CTGGAACTAA TTCTTCTCAA GAACCTATTG AAAATGGTTT ACCAAAGACT
1081 GGTGTTTATA ATATTATCGG AAGTACTGAA GTAAAAAATG AAGCTAAAAT ATCAAGTCAG
1141 ACCCAATTTA CTTTAGAAAA AGGTGACAAA ATAAATTATG ATCAAGTATT GACAGCAGAT
1201 GGTTACCAGT GGATTTCTTA CAAATCTTAT AGTGGTGTTC GTCGCTATAT TCCTGTGAAA
1261 AAGCTAACTA CAAGTAGTGA AAAAGCGAAA GATGAGGCGA CTAAACCGAC TAGTTATCCC
1321 AACTTACCTA AAACAGGTAC CTATACATTT ACTAAAACTG TAGATGTGAA AAGTCAACCT
1381 AAAGTATCAA GTCCAGTGGA ATTAATTTT CAAAAGGGTG AAAAAATACA TTATGATCAA
1441 GTGTTAGTAG TAGATGGTCA TCAGTGGATT TCATACAAGA GTTATTCCGG TATTCGTCGC
1501 TATATTGAAA TTTAA
```

Figure 3 (SEQ ID NO: 3)

```
  1 MRGSLSTKQS YSLRKYKFGL ASVILGSFIM VTSPVFADQT TSVQVNNQTG TSVDANNSSN
 61 ETSASSVITS NNDSVQASDK VVNSQNTATK DITTPLVETK PMVEKTLPEQ GNYVYSKETE
121 VKNTPSKSAP VAFYAKKGDK VFYDQVFNKD NVKWISYKSF GGVRRYAAIE SLDPSGGSET
181 KAPTPVTNSG SNNQEKIATQ GNYTFSHKVE VKNEAKVASP TQFTLDKGDR IFYDQILTIE
241 GNQWLSYKSF NGVRRFVLLG KASSVEKTED KEKVSPQPQA RITKTGRLTI SNETTTGFDI
301 LITNIKDDNG IAAVKVPVWT EQGGQDDIKW YTAVTTGDGN YKVAVSFADH KNEKGLYNIH
361 LYYQEASGTL VGVTGTKVTV AGTNSSQEPI ENGLPKTGVY NIIGSTEVKN EAKISSQTQF
421 TLEKGDKINY DQVLTADGYQ WISYKSYSGV RRYIPVKKLT TSSEKAKDEA TKPTSYPNLP
481 KTGTYTFTKT VDVKSQPKVS SPVEFNFQKG EKIHYDQVLV DGHQWISYK SYSGIRRYIE
541 I*
```

Figure 4 (SEQ ID NO: 4)

```
  1 DQTTSVQVNN QTGTSVDANN SSNETSASSV ITSNNDSVQA SDKVVNSQNT ATKDITTPLV
 61 ETKPMVEKTL PEQGNYVYSK ETEVKNTPSK SAPVAFYAKK GDKVFYDQVF NKDNVKWISY
121 KSFGGVRRYA AIESLDPSGG SETKAPTPVT NSGSNNQEKI ATQGNYTFSH KVEVKNEAKV
181 ASPTQFTLDK GDRIFYDQIL TIEGNQWLSY KSFNGVRRFV LLGKASSVEK TEDKEKVSPQ
241 PQARITKTGR LTISNETTTG FDILITNIKD DNGIAAVKVP VWTEQGGQDD IKWYTAVTTG
301 DGNYKVAVSF ADHKNEKGLY NIHLYYQEAS GTLVGVTGTK VTVAGTNSSQ EPIENGLPKT
361 GVYNIIGSTE VKNEAKISSQ TQFTLEKGDK INYDQVLTAD GYQWISYKSY SGVRRYIPVK
421 KLTTSSEKAK DEATKPTSYP NLPKTGTYTF TKTVDVKSQP KVSSPVEFNF QKGEKIHYDQ
481 VLVVDGHQWI SYKSYSGIRR YIEI*
```

Figure 5 (SEQ ID NO: 5)

```
   1 ATGAAGATTA AAAAAATTAT TAGTGGCTTT GCCGCAGCTT TAATTATCAG TTCACTATCA
  61 ACTATTAACT ATGAGGTTAA AGCTGATGAC ACCACCAGTG AGTATCACTA TATCAGTAAG
 121 CAAAATAATG AAAAGCAGCT TATTAGTTAC ATCAAGGAAC AACATCGTTT GCTCAATCAA
 181 TTTGTTGTTG ATAATGTCAA CTCATTCACT CAACTAAATG CTAATCCAAC TATTGAACAG
 241 TTAAATAGAG CTATAACATT ATTTAAACAA AAAGATGAGC AATTATTTAA CCAGGTGAAA
 301 GCTGGTCATC TCTCTCCCAG TAACTATAAT GCTATCGTTA ATCAACGTAA TGTCATTAAC
 361 CAAACTGTTC AAAATCTGAT TGACCAAAAT CATAATAAGA TTCAGACAAG TCAAAATAAA
 421 GCAGCTCAGC TCGTGGGGCA ACGTAATCAG GTTGTTAACA AAATTCAAGC TATTTTAGCA
 481 ACTGTAAACT ACAACTCTGT GAATTCTATA CAAGAAGCTG AAAATTTATT TCATTCACTC
 541 AGAAATCAAA TTGAACCTCT TGTAGCTGAA GTTAATAATT ACAAAGCTGC TATGGCAATC
 601 CTTCAACAAG AAGTAGATGC CCTATCAACA GCGGCTATTG AAACTGAGAC TTCTAAACTT
 661 GCTACTCTCA AGTTAGCGA AAATACTTCT GTTCCTGCAA ACAAAGTAGA AGAAAAAACT
 721 ACTCAATCAG AAGCGTCAGG CAATAAACAA GAAGTAACTA AGAGTGAGGA AAAACAGGCT
 781 ACCTCTGATG CAAAGGCATC ACAGCCTGAG TCAGCTAATA TTGCCGATTA CGATAGTTTA
 841 AAAGAAGTTT TACGAAATAA TATTAGCAAC CAAGTACCAC ACATCAGTGT TCAAATGGAG
 901 TTTAAAACTC AAGAACAAGT TGACGAATAC CAAAAAAATC TCGGAAGCAT CATCCGGGAA
 961 ATTGGAGATA CACTTGGAAC AGCAACTGAA TTCAATGCCA AAAGTAACAT TAGCACTTAT
1021 ACTCTTGGTG ACAAATCCA ACGCATTATT GTAAAAGCG ACATCACAAT CACCTATACT
1081 CTTAAAGGTG ACATGGTAGG ATTACATAAA GAATATAAAC AGTTTGTAGA TTCTTTTGTC
1141 AAAGAAAATA TTACTAACAA AAATATCACA AGTGATTATG AAAAAGCTAA AGTAATTCAT
1201 GACCACTTGG TTAATAATTA CACTTACGCG ACTGAAGAAC TGCAACCAC TCGTGAAACT
1261 GCTAGTGGTA TCAGTATCCA TGCTCCTGAA GCACTCTACA AGATAAACG TGGTGTTTGT
1321 CAAGCCTTTG CAGTAATGTT TAAAGATATG GCTGCTGCTG CTTATCAGT ATGGTATGTA
1381 ACTGGTCAAG CTGGAGGTGG AAATCACGCT TGGAACATTG TTACTATTAA TGGCGTTAAA
1441 TATTATGTTG ATACAACATG GATAATAAT ATAAAAGCA ATAAATATTT CCTTGTTGGT
1501 AAAACAATAA TGGATGCTGA TCATCTTTTG GATAGTCAAT ACAATGCATT AGCTAAAGAT
1561 ATTCCAGCTG ATCGCCATCA AGGTGCATAA
```

Figure 6 (SEQ ID NO: 6)

```
   1 GATGACACCA CCAGTGAGTA TCACTATATC AGTAAGCAAA ATAATGAAAA GCAGCTTATT
  61 AGTTACATCA AGGAACAACA TCGTTTGCTC AATCAATTTG TTGTTGATAA TGTCAACTCA
 121 TTCACTCAAC TAAATGCTAA TCCAACTATT GAACAGTTAA ATAGAGCTAT AACATTATTT
 181 AAACAAAAAG ATGAGCAATT ATTTAACCAG GTGAAAGCTG GTCATCTCTC TCCCAGTAAC
 241 TATAATGCTA TCGTTAATCA ACGTAATGTC ATTAACCAAA CTGTTCAAAA TCTGATTGAC
 301 CAAAATCATA ATAAGATTCA GACAAGTCAA AATAAAGCAG CTCAGCTCGT GGGGCAACGT
 361 AATCAGGTTG TTAACAAAAT TCAAGCTATT TTAGCAACTG TAAACTACAA CTCTGTGAAT
 421 TCTATACAAG AAGCTGAAAA TTTATTTCAT TCACTCAGAA ATCAAATTGA ACCTCTTGTA
 481 GCTGAAGTTA ATAATTACAA AGCTGCTATG GCAATCCTTC AACAAGAAGT AGATGCCCTA
 541 TCAACAGCGG CTATTGAAAC TGAGACTTCT AAACTTGCTA CTCTCAAAGT TAGCGAAAAT
 601 ACTTCTGTTC CTGCAAACAA AGTAGAAGAA AAAACTACTC AATCAGAAGC GTCAGGCAAT
 661 AAACAAGAAG TAACTAAGAG TGAGGAAAAA CAGGCTACCT CTGATGCAAA GGCATCACAG
 721 CCTGAGTCAG CTAATATTGC CGATTACGAT AGTTTAAAAG AAGTTTTACG AAATAATATT
 781 AGCAACCAAG TACCACACAT CAGTGTTCAA ATGGAGTTTA AAACTCAAGA ACAAGTTGAC
 841 GAATACCAAA AAAATCTCGG AAGCATCATC CGGGAAATTG GAGATACACT TGGAACAGCA
 901 ACTGAATTCA ATGCCAAAAG TAACATTAGC ACTTATACTC TTGGTGGACA AATCCAACGC
 961 ATTATTGTAA AAAGCGACAT CACAATCACC TATACTCTTA AGGTGACATG GTAGGATTA
1021 CATAAAGAAT ATAAACAGTT TGTAGATTCT TTTGTCAAAG AAAATATTAC TAACAAAAAT
1081 ATCACAAGTG ATTATGAAAA AGCTAAAGTA ATTCATGACC ACTTGGTTAA TAATTACACT
1141 TACGCGACTG AAGAACTGGC AACCACTCGT GAAACTGCTA GTGGTATCAG TATCCATGCT
1201 CCTGAAGCAC TCTACAAAGA TAAACGTGGT GTTTGTCAAG CCTTTGCAGT AATGTTTAAA
1261 GATATGGCTG CTGCTGGCTT ATCAGTATGG TATGTAACTG GTCAAGCTGG AGGTGGAAAT
1321 CACGCTTGGA ACATTGTTAC TATTAATGGC GTTAAATATT ATGTTGATAC AACATGGGAT
1381 AATAATATAA AAAGCAATAA ATATTTCCTT GTTGGTAAAA CAATAATGGA TGCTGATCAT
1441 CTTTTGGATA GTCAATACAA TGCATTAGCT AAAGATATTC CAGCTGATCG CCATCAAGGT
1501 GCATAA
```

Figure 7 (SEQ ID NO: 7)

```
  1 MKIKKIISGF AAALIISSLS TINYEVKADD TTSEYHYISK QNNEKQLISY IKEQHRLLNQ
 61 FVVDNVNSFT QLNANPTIEQ LNRAITLFKQ KDEQLFNQVK AGHLSPSNYN AIVNQRNVIN
121 QTVQNLIDQN HNKIQTSQNK AAQLVGQRNQ VVNKIQAILA TVNYNSVNSI QEAENLFHSL
181 RNQIEPLVAE VNNYKAAMAI LQQEVDALST AAIETETSKL ATLKVSENTS VPANKVEEKT
241 TQSEASGNKQ EVTKSEEKQA TSDAKASQPE SANIADYDSL KEVLRNNISN QVPHISVQME
301 FKTQEQVDEY QKNLGSIIRE IGDTLGTATE FNAKSNISTY TLGGQIQRII VKSDITITYT
361 LKGDMVGLHK EYKQFVDSFV KENITNKNIT SDYEKAKVIH DHLVNNYTYA TEELATTRET
421 ASGISIHAPE ALYKDKRGVC QAFAVMFKDM AAAGLSVWYV TGQAGGGNHA WNIVTINGVK
481 YYVDTTWDNN IKSNKYFLVG KTIMDADHLL DSQYNALAKD IPADRHQGA*
```

Figure 8 (SEQ ID NO: 8)

```
  1 DDTTSEYHYI SKQNNEKQLI SYIKEQHRLL NQFVVDNVNS FTQLNANPTI EQLNRAITLF
 61 KQKDEQLFNQ VKAGHLSPSN YNAIVNQRNV INQTVQNLID QNHNKIQTSQ NKAAQLVGQR
121 NQVVNKIQAI LATVNYNSVN SIQEAENLFH SLRNQIEPLV AEVNNYKAAM AILQQEVDAL
181 STAAIETETS KLATLKVSEN TSVPANKVEE KTTQSEASGN KQEVTKSEEK QATSDAKASQ
241 PESANIADYD SLKEVLRNNI SNQVPHISVQ MEFKTQEQVD EYQKNLGSII REIGDTLGTA
301 TEFNAKSNIS TYTLGGQIQR IIVKSDITIT YTLKGDMVGL HKEYKQFVDS FVKENITNKN
361 ITSDYEKAKV IHDHLVNNYT YATEELATTR ETASGISIHA PEALYKDKRG VCQAFAVMFK
421 DMAAAGLSVW YVTGQAGGGN HAWNIVTING VKYYVDTTWD NNIKSNKYFL VGKTIMDADH
481 LLDSQYNALA KDIPADRHQG A*
```

BVH-A2 AND BVH-A3 ANTIGENS OF GROUP B STREPTOCOCCUS

This application claims the benefit of U.S. provisional application Ser. No. 60/239,919, filed Oct. 13, 2000.

FIELD OF THE INVENTION

The present invention is related to polypeptides of Group B *Streptococcus* (GBS) (*S. agalactiae*) and corresponding DNA fragments, which may be useful to prevent, diagnose and/or treat GBS infections in individuals such as humans.

BACKGROUND OF THE INVENTION

*Streptococcus* are gram (+) bacteria that are differentiated by group specific carbohydrate antigens A through O found on their cell surface. *Streptococcus* groups are further distinguished by type-specific capsular polysaccharide antigens. Several serotypes have been identified for the GBS: Ia, Ib, II, III, IV, V, VI, VII and VIII. GBS also contains antigenic proteins known as "C-proteins" (alpha, beta, gamma and delta), some of which have been cloned.

Although GBS is a common component of the normal human vaginal and colonic flora this pathogen has long been recognized as a major cause of infections in neonates, expectant mothers, some non-pregnant adults as well as mastitis in dairy herds. Expectant mothers exposed to GBS are at risk of postpartum infection and may transfer the infection to their baby as the child passes through the birth canal.

GBS infections in infants are restricted to very early infancy. Approximately 80% of infant infections occur in the first days of life, so-called early-onset disease. Late-onset infections occur in infants between 1 week and 2 to 3 months of age. Clinical syndromes of GBS disease in newborns include sepsis, meningitis, pneumonia, cellulitis, osteomyelitis, septic arthritis, endocarditis, epiglottis. In addition to acute illness due to GBS, which is itself costly, GBS infections in newborns can result in death, disability, and, in rare instances, recurrence of infection. Although the organism is sensitive to antibiotics, the high attack rate and rapid onset of sepsis in neonates and meningitis in infants results in high morbidity and mortality.

Among pregnant women, GBS causes clinical illness ranging from mild urinary tract infection to life-threatening sepsis and meningitis, including also osteomyelitis, endocarditis, amniotis, endometritis, wound infections (postcesarean and postepisiotomy), cellulitis, fasciitis.

Among non-pregnant adults, the clinical presentations of invasive GBS disease most often take the form of primary bacteremia but also skin of soft tissue infection, pneumonia, urosepsis, endocarditis, peritonitis, meningitis, empyema. Skin of soft tissue infections include cellulitis, infected peripheral ulcers, osteomyelitis, septic arthritis and decubiti or wound infections. Among people at risk, there are debilitated hosts such as people with a chronic disease such as diabetes mellitus and cancer, or elderly people.

GBS infections can also occur in animals and cause mastitis in dairy herds.

To find a vaccine that will protect hosts from GBS infection, researches have turned to the type-specific antigens. Unfortunately these polysaccharides have proven to be poorly immunogenic in hosts and are restricted to the particular serotype from which the polysaccharide originates. Further, capsular polysaccharide elicit a T cell independent response i.e. no IgG production. Consequently capsular polysaccharide antigens are unsuitable as a vaccine component for protection against GBS infection.

Others have focused on the C-protein beta antigen which demonstrated immunogenic properties in mice and rabbit models. This protein was found to be unsuitable as a human vaccine because of its undesirable property of interacting with high affinity and in a non-immunogenic manner with the Fc region of human IgA. The C-protein alpha antigen is rare in type III serotypes of GBS which is the serotype responsible for most GBS mediated conditions and is therefore of little use as a vaccine component.

There remains an unmet need for GBS polypeptides that may be useful to prevent, diagnose and/or treat GBS infections in individuals such as humans.

SUMMARY OF THE INVENTION

According to one aspect, the present invention provides an isolated polynucleotide encoding a polypeptide having at least 70% identity to a second polypeptide comprising a sequence chosen from SEQ ID NOS: 3, 4, 7 and 8 or fragments or analogs thereof.

According to one aspect, the present invention relates to polypeptides which comprise an amino acid sequence selected from SEQ ID NOS: 3, 4, 7 and 8 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and processes of producing polypeptides comprising culturing said host cells under conditions suitable for expression.

BRIEF DESCRIPTION OF THE DRAWINGS

FIG. 1 represents the DNA sequence of BVH-A2 gene from serotype III Group B *streptococcus* strain NCS954; SEQ ID NO: 1.

FIG. 2 represents the DNA sequence of BVH-A2 gene from serotype III Group B *streptococcus* strain NCS954 without the region coding for its leader peptide; SEQ ID NO: 2.

FIG. 3 represents the amino acid sequence of BVH-A2polypeptide from serotype III Group B *streptococcus* strain NCS954; SEQ ID NO: 3.

FIG. 4 represents the amino acid sequence of BVH-A2 polypeptide from serotype III Group B *streptococcus* strain NCS954 without the 37 amino acid residues leader peptide; SEQ ID NO: 4.

FIG. 5 represents the DNA sequence of BVH-A3 gene from serotype III Group B *streptococcus* strain NCS954; SEQ ID NO: 5.

FIG. 6 represents the DNA sequence of BVH-A3 gene from serotype III Group B *streptococcus* strain NCS954 without the region coding for the leader peptide; SEQ ID NO: 6.

FIG. 7 represents the amino acid sequence of BVH-A3 polypeptide from serotype III Group B *streptococcus* strain NCS954; SEQ ID NO: 7.

FIG. 8 represents the amino acid sequence of BVH-A3 polypeptide from serotype III Group B *streptococcus* strain NCS954 without the 2 amino acid residues leader peptide; SEQ ID NO: 8.

DETAILED DESCRIPTION OF THE INVENTION

The present invention provides purified and isolated polynucleotides, which encode Group B Streptococcal polypeptides that may be used to prevent, treat, and/or diagnose streptococcal infection. The present invention provides four separate preferred polynucleotides, each individually and separately defined by one of SEQ ID NOS 1, 2, 5 and 6. Further provided in the present invention are four separate polypeptides, each individually and separately defined by one of seq ID NOS: 3, 4, 7 and 8. Those skilled in the art will appreciate that the invention includes polynucleotides that encode analogs such as mutants, variants, homologues and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

According to one aspect, the present invention provides an isolated polynucleotide encoding a polypeptide having at least 70% identity to a second polypeptide comprising a sequence chosen from SEQ ID NOS: 3, 4, 7 and 8 or fragments or analogs thereof.

According to one aspect, the present invention provides an isolated polynucleotide encoding a polypeptide having at least 80% identity to a second polypeptide comprising a sequence chosen from SEQ ID NOS: 3, 4, 7 and 8 or fragments or analogs thereof.

According to one aspect, the present invention provides an isolated polynucleotide encoding a polypeptide having at least 85% identity to a second polypeptide comprising a sequence chosen from SEQ ID NOS: 3, 4, 7 and 8 or fragments or analogs thereof.

According to one aspect, the present invention provides an isolated polynucleotide encoding a polypeptide having at least 90% identity to a second polypeptide comprising a sequence chosen from SEQ ID NOS: 3, 4, 7 and 8 or fragments or analogs thereof.

According to one aspect, the present invention provides an isolated polynucleotide encoding a polypeptide having at least 95% identity to a second polypeptide comprising a sequence chosen from SEQ ID NOS: 3, 4, 7 and 8 or fragments or analogs thereof.

According to one aspect, the present invention provides an isolated polynucleotide encoding a polypeptide comprising a sequence chosen from SEQ ID NOS: 3, 4, 7 and 8 or fragments or analogs thereof.

According to one aspect, the present invention relates to polynucleotides encoding an epitope bearing portion of a polypeptide having a sequence chosen from SEQ ID NOS: 3, 4, 7 and 8 or fragments or analogs thereof.

According to one aspect, the present invention relates to epitope bearing portions of a polypeptide having a sequence chosen from SEQ ID NOS: 3, 4, 7 and 8 or fragments or analogs thereof.

According to one aspect, the present invention relates to polypeptides comprising an amino acid sequence comprising sequences from SEQ ID NOS: 3, 4, 7 and 8 or fragments or analogs thereof.

According to one aspect, the present invention provides an isolated polynucleotide encoding a polypeptide having at least 70% identity to a second polypeptide comprising a sequence chosen from SEQ ID NOS: 3, 4, 7 and 8.

According to one aspect, the present invention provides an isolated polynucleotide encoding a polypeptide having at least 80% identity to a second polypeptide comprising a sequence chosen from SEQ ID NOS: 3, 4, 7 and 8.

According to one aspect, the present invention provides an isolated polynucleotide encoding a polypeptide having at least 85% identity to a second polypeptide comprising a sequence chosen from SEQ ID NOS: 3, 4, 7 and 8.

According to one aspect, the present invention provides an isolated polynucleotide encoding a polypeptide having at least 90% identity to a second polypeptide comprising a sequence chosen from SEQ ID NOS: 3, 4, 7 and 8.

According to one aspect, the present invention provides an isolated polynucleotide encoding a polypeptide having at least 95% identity to a second polypeptide comprising a sequence chosen from SEQ ID NOS: 3, 4, 7 and 8.

According to one aspect, the present invention provides an isolated polynucleotide encoding a polypeptide comprising a sequence chosen from SEQ ID NOS: 3, 4, 7 and 8.

According to one aspect, the present invention relates to polynucleotides encoding an epitope bearing portion of a polypeptide having a sequence chosen from SEQ ID NOS: 3, 4, 7 and 8.

According to one aspect, the present invention relates to epitope bearing portions of a polypeptide having a sequence chosen from SEQ ID NOS: 3, 4, 7 and 8.

In a further embodiment, the present invention also relates to polynucleotides encoding a polypeptide which is able to raise antibodies having binding specificity for a polypeptide having a sequence chosen from SEQ ID NOS: 3, 4, 7 and 8 or fragments or analogs thereof.

In a further embodiment, the present invention also relates to polynucleotides encoding a polypeptide which is able to raise antibodies having binding specificity for a polypeptide having a sequence chosen from SEQ ID NOS: 3, 4, 7 and 8.

The percentage of homology is defined as the sum of the percentage of identity plus the percentage of similarity or conservation of amino acid type.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a individual.

In a further embodiment, the present invention also relates to polypeptides which are able to raise antibodies having binding specificity to the polypeptides of the present invention as defined above.

In a further embodiment, the present invention also relates to polypeptides which are able to raise antibodies having binding specificity for a polypeptide having a sequence chosen from SEQ ID NOS: 3, 4, 7 and 8 or fragments or analogs thereof.

In a further embodiment, the present invention also relates to polypeptides which are able to raise antibodies having binding specificity for a polypeptide having a sequence chosen from SEQ ID NOS: 3, 4, 7 and 8.

An antibody that "has binding specificity" is an antibody that recognises and binds the selected polypeptide but which does not substantially recognise and bind other molecules in a sample, e.g., a biological sample which naturally includes the selected peptide. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that "fragments", "analogs" or "derivatives" of the polypeptides of the invention will also find use in the context of the present invention, i.e. as antigenic/immunogenic material. Thus, for instance polypeptides which include one or more additions, deletions, substitutions or the like are encompassed by the present invention.

As used herein, "analogs" of the polypeptides of the invention include those polypeptides in which one or more of the amino acid residues are substituted with a conserved amino acid residue (preferably conserved) and which may be natural or unnatural. In one embodiment, analogs of polypeptides of the invention will have about 70% identity with those sequences illustrated in the figures or fragments thereof. That is, 70% of the residues are the same. In a further embodiment, polypeptides will have greater than 80% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

In one embodiment, derivatives and analogs of polypeptides of the invention will have about 70% homology with those sequences illustrated in the figures or fragments thereof. In a further embodiment, derivatives and analogs of polypeptides will have greater than 80% homology. In a further embodiment, derivatives and analogs of polypeptides will have greater than 90% homology. In a further embodiment, derivatives and analogs of polypeptides will have greater than 95% homology. In a further embodiment, derivatives and analogs of polypeptides will have greater than 99% homology. In a further embodiment, derivatives and analogs of derivatives and analogs of polypeptides of the invention will have fewer than about 20 amino acid residue substitutions, modifications or deletions and more preferably less than 10.

According to a further aspect, the invention provides polypeptides having at least 70% identity to a second polypeptide having an amino acid sequence chosen from: SEQ ID NOS: 3, 4, 7 and 8 or fragments or analogs thereof.

According to a further aspect, the invention provides polypeptides having at least 80% identity to a second polypeptide having an amino acid sequence chosen from: SEQ ID NOS: 3, 4, 7 and 8 or fragments or analogs thereof.

According to a further aspect, the invention provides polypeptides having at least 85% identity to a second polypeptide having an amino acid sequence chosen from: SEQ ID NOS: 3, 4, 7 and 8 or fragments or analogs thereof.

According to a further aspect, the invention provides polypeptides having at least 90% identity to a second polypeptide having an amino acid sequence chosen from: SEQ ID NOS: 3, 4, 7 and 8 or fragments or analogs thereof.

According to a further aspect, the invention provides polypeptides having at least 95% identity to a second polypeptide having an amino acid sequence chosen from: SEQ ID NOS: 3, 4, 7 and 8 or fragments or analogs thereof.

According to a further aspect, the invention provides polypeptides comprising a sequence chosen from: SEQ ID NOS: 3, 4, 7 and 8 or fragments or analogs thereof.

According to a further aspect, the invention provides polypeptides characterized by a sequence chosen from: SEQ ID NOS: 3, 4, 7 and 8 or fragments or analogs thereof.

According to a further aspect, the invention provides polypeptides having at least 70% identity to a second polypeptide having an amino acid sequence chosen from: SEQ ID NOs: 3, 4, 7 and 8.

According to a further aspect, the invention provides polypeptides having at least 80% identity to a second polypeptide having an amino acid sequence chosen from: SEQ ID NOS: 3, 4, 7 and 8.

According to a further aspect, the invention provides polypeptides having at least 85% identity to a second polypeptide having an amino acid sequence chosen from: SEQ ID NOS: 3, 4, 7 and 8.

According to a further aspect, the invention provides polypeptides having at least 90% identity to a second polypeptide having an amino acid sequence chosen from: SEQ ID NOS: 3, 4, 7 and 8.

According to a further aspect, the invention provides polypeptides having at least 95% identity to a second polypeptide having an amino acid sequence chosen from: SEQ ID NOS: 3, 4, 7 and 8.

According to a further aspect, the invention provides polypeptides comprising a sequence chosen from: SEQ ID NOS: 3, 4, 7 and 8.

According to a further aspect, the invention provides polypeptides characterized by a sequence chosen from: SEQ ID NOS: 3, 4, 7 and 8.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:
ala, pro, gly, gln, asn, ser, thr, val;
cys, ser, tyr, thr;
val, ile, leu, met, ala, phe;
lys, arg, orn, his;
and phe, tyr, trp, his.

The preferred substitutions also include substitutions of D-enantiomers for the corresponding L-amino acids.

Preferably, a fragment, analog or derivative of a polypeptide of the invention will comprise at least one antigenic region i.e. at least one epitope.

In an alternative approach, the analogs could be fusion polypeptides, incorporating moieties which render purification easier, for example by effectively tagging the desired polypeptide. It may be necessary to remove the "tag" or it may be the case that the fusion polypeptide itself retains sufficient antigenicity to be useful.

Thus, what is important for analogs, derivatives and fragments is that they possess at least a degree of the antigenicity/immunogenicity of the polypeptides of the invention from which they are derived.

Also included are polypeptides which have fused thereto other compounds which alter the biological or pharmacological properties of the polypeptide, i.e., polyethylene glycol (PEG) to increase half-life, leader or secretory amino acid sequences for ease of purification, prepro- and pro-sequences and (poly)saccharides.

Furthermore, in those situations where amino acid regions are found to be polymorphic, it may be desirable to vary one or more particular amino acids to more effectively mimic the different epitopes of the different GBS strains.

Moreover, the polypeptides of the present invention can be modified by terminal —$NH_2$ acylation (e.g. by acetylation or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogues. These polymeric forms include, for example, one or more polypeptides that have been cross-linked with cross-linkers such as avidin/biotin, glutaraldehyde or dimethylsuperimidate. Such polymeric forms also include polypeptides containing two or more tandem or inverted contiguous sequences, produced from multicistronic mRNAs generated by recombinant DNA technology.

In a further embodiment, the present invention also relates to chimeric polypeptides which comprise one or more polypeptides or fragments or analogs or derivatives thereof as defined in the figures of the present application.

In a further embodiment, the present invention also relates to chimeric polypeptides comprising two or more polypeptides having a sequence chosen from SEQ ID NOS: 3, 4, 7 and 8 or fragments or analogs thereof; provided that the polypeptides are linked as to formed a chimeric polypeptide.

In a further embodiment, the present invention also relates to chimeric polypeptides comprising two or more polypeptides having a sequence chosen from SEQ ID NOS: 3, 4, 7 and 8 provided that the polypeptides are linked as to formed a chimeric polypeptide.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different peptides may be a single bound or may be composed of a linking group of at least two, typically at least four and not more than 16, but usually not more than about 14 carbon atoms.

In a particular embodiment, polypeptide fragments or analogs of the invention do not contain a methionine (Met) starting residue. Preferably, polypeptides will not incorporate a leader or secretory sequence (signal sequence). The signal portion of a polypeptide of the invention may be determined according to established molecular biological techniques. In general,the polypeptide of interest may be isolated from GBS culture and subsequently sequenced to determine the initial residue of the mature protein and therefore the sequence of the mature polypeptide.

According to another aspect of the invention, there are also provided (i) a composition of matter containing a polypeptide of the invention, together with a carrier, diluent or adjuvant; (ii) a pharmaceutical composition comprising a polypeptide of the invention and a carrier, diluent or adjuvant; (iii) a vaccine comprising a polypeptide of the invention and a carrier, diluent or adjuvant; (iv) a method for inducing an immune response against GBS, in an individual, by administering to the individual, an immunogenically effective amount of a polypeptide of the invention to elicit an immune response, e.g., a protective immune response to GBS; and particularly, (v) a method for preventing and/or treating a GBS infection, by administering a prophylactic or therapeutic amount of a polypeptide of the invention to an individual in need.

Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol.19 (ed.) Burdou, R. H. & Van Knippenberg P. H. (1988), Elsevier New York.

According to another aspect, there are provided pharmaceutical compositions comprising one or more GBS polypeptides of the invention in a mixture with a pharmaceutically acceptable carrier diluent or adjuvant. Suitable adjuvants include (1) oil-in-water emulsion formulations such as MF59™, SAF™, Ribi™; (2) Freund's complete or incomplete adjuvant; (3) salts i.e. $AlK(SO_4)_2$, $AlNa(SO_4)_2$, $AlNH_4(SO_4)_2$, $Al(OH)_3$, $AlPO_4$, silica, kaolin; (4) saponin derivatives such as Stimulon™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides i.e. poly IC and poly AU, detoxified cholera toxin (CTB) and E.coli heat labile toxin for induction of mucosal immunity. A more detailed description of adjuvant is available in a review by M. Z. I Khan et al. in Pharmaceutical Research, vol. 11, No. 1 (1994) pp 2-11, and also in another review by Gupta et al., in Vaccine, Vol. 13, No. 14, pp 1263-1276 (1995) and in WO 99/24578. Preferred adjuvants include QuilA™, QS21™, Alhydrogel™ and Adjuphos™.

Pharmaceutical compositions of the invention may be administered parenterally by injection, rapid infusion, nasopharyngeal absorption, dermoabsorption, or buccal or oral.

Pharmaceutical compositions of the invention are used for the treatment or prophylaxis of streptococcal infection and/or diseases and symptoms mediated by streptococcal infection, in particular Group A *streptococcus* (*S.pyogenes*), Group B *streptococcus* (GBS or *S.agalactiae*), *S.dysgalactiae*, *S.uberis*, *S.nocardia* as well as *Staphylococcus aureus*. General information about *Streptococcus*, and more particularly GBS, is available in Manual of Clinical Microbiology by P. R. Murray et al. (1995, 6$^{th}$ Edition, ASM Press, Washington, D.C.).

In one embodiment, pharmaceutical compositions of the invention are used for the treatment or prophylaxis of GBS infection and/or diseases and symptoms mediated by GBS infection.

In a particular embodiment, pharmaceutical compositions of the invention are administered to those individuals at risk of GBS infection such as pregnant women for mild urinary tract infection to life-threatening sepsis and meningitis, including also osteomyelitis, endocarditis, amniotis, endometritis, wound infections (postcesarean and postepisiotomy), cellulitis, fasciitis.

In a particular embodiment, pharmaceutical compositions of the invention are administered to those individuals at risk of GBS infection such as neonates and infants for sepsis, meningitis, pneumonia, cellulitis, osteomyelitis, septic arthritis, endocarditis, epiglottis.

In a particular embodiment, pharmaceutical compositions of the invention are administered to those individuals at risk of GBS infection such as non-pregnant adults, for primary bacteremia but also skin of soft tissue infection, pneumonia, urosepsis, endocarditis, peritonitis, meningitis, empyema. Skin of soft tissue infections include cellulitis, infected peripheral ulcers, osteomyelitis, septic arthritis and decubiti or wound infections. Among people at risk, there are debilitated individuals such as people with a chronic disease such as diabetes mellitus and cancer, or elderly people.

In a particular embodiment, pharmaceutical compositions of the invention are administered to those individuals at risk of GBS infection such as cattle for the treatment of mastitis in cattle.

In a further aspect, the invention provides the use of pharmaceutical composition of the invention for the prophylactic or therapeutic treatment of GBS bacterial infection in an individual susceptible to GBS infection comprising administering to said individual a therapeutic or prophylactic amount of a composition of the invention.

According to a further aspect, the GBS polypeptides of the invention may be used in a kit comprising the polypeptides of the invention for detection of diagnosis of GBS infection.

As used in the present application, the term "individual" include mammals. In a further embodiment, the mammals are humans. In a further embodiment, the mammals are non-humans, such as herds.

In a particular embodiment, pharmaceutical compositions of the invention are administered to those individuals at risk of GBS infection such as neonates.

Pharmaceutical compositions of the invention are preferably in unit dosage form of about 0.001 to 100 μg/kg (antigen/body weight) and more preferably 0.01 to 10 μg/kg and most preferably 0.1 to 1 μg/kg, 1 to 3 times with an interval of about 1 to 6 week intervals between immunisations.

Pharmaceutical compositions are preferably in unit dosage form of about 0.1 μg to 10 mg and more preferably 1 μg to 1 mg and most preferably 10 to 100 μg 1 to 3 times with an interval of about 1 to 6 week intervals between immunizations.

In one embodiment, polynucleotides are those illustrated in SEQ ID NOS: 1, 2, 5 and 6 which may include the open reading frames (ORF), encoding the polypeptides of the invention.

In one embodiment, polynucleotides are those illustrated in SEQ ID NOS: 1, 2, 5 and 6 encoding the polypeptides of the invention.

It will be appreciated that the polynucleotide sequences illustrated in the figures may be altered with degenerated codons yet still encode the polypeptides of the invention. Accordingly the present invention further provides polynucleotides herein above described (or the complement sequence thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions, i.e. having at least 95% identity. In a further embodiment, more than 97% identity.

Suitable stringent conditions for hybridation can be readily determined by one of skilled in the art (see for example Sambrook et al., (1989) Molecular cloning: A Laboratory Manual, 2$^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either (a) a polynucleotide encoding a polypeptide or
(b) the complement of a polynucleotide encoding a polypeptide;

wherein said polypeptide comprises SEQ ID NO: 3, 4, 7 and 8, or fragments or analogs thereof.

In a further embodiment, the present invention provides polynucleotides that hybridize under stringent conditions to either (a) a polynucleotide encoding a polypeptide or
(b) the complement of a polynucleotide encoding a polypeptide;

wherein said polypeptide comprises at least 10 contiguous amino acid residues from a polypeptide comprising SEQ ID NO: 3, 4, 7 and 8 or fragments or analogs thereof.

In a further embodiment, the present invention provides polynucleotides that hybridize under stringent conditions to either (a) a polynucleotide encoding a polypeptide or
(b) the complement of a polynucleotide encoding a polypeptide;

wherein said polypeptide comprises SEQ ID NO: 3, 4, 7 and 8.

In a further embodiment, the present invention provides polynucleotides that hybridize under stringent conditions to either (a) a polynucleotide encoding a polypeptide or
(b) the complement of a polynucleotide encoding a polypeptide;

wherein said polypeptide comprises at least 10 contiguous amino acid residues from a polypeptide comprising SEQ ID NO: 3, 4, 7 and 8.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments or analogs thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably, the vector is injected intramuscularly.

According to another aspect, there is provided a process or method of manufacturing for producing polypeptides of the invention by recombinant techniques by expressing a polynucleotide encoding said polypeptide in a host cell and recovering the expressed polypeptide product. Alternatively, the polypeptides can be produced according to established synthetic chemical techniques, i.e. solution phase or solid phase synthesis of oligopeptides which are ligated to produce the full polypeptide (block ligation).

General methods for obtention and evaluation of polynucleotides and polypeptides are described in the following references: Sambrook et al., (1989) Molecular cloning: A Laboratory Manual, 2$^{nd}$ ed, Cold Spring Harbor, N.Y.; Current Protocols in Molecular Biology, (1999) Edited by Ausubel F. M. et al., John Wiley & Sons, Inc., N.Y.; PCR Cloning Protocols, from Molecular Cloning to Genetic Engineering, (1997) Edited by White B. A., Humana Press, Totowa, N.J., 490 pages; Protein Purification, Principles and Practices, (1993) Scopes R. K., Springer-Verlag, N.Y., 3$^{rd}$ Edition, 380 pages; Current Protocols in Immunology, (1999) Edited by Coligan J. E. et al., John Wiley & Sons Inc., N.Y., are herein incorporated by reference.

For recombinant production, host cells are transfected with vectors which encode the polypeptides, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al., (1989) Molecular Cloning: A Laboratory manual, 2$^{nd}$ ed., Cold Spring Harbor, N.Y.; Current Protocols in Molecular Biology, (1999) Edited by Ausubel F. M. et al., John Wikey & Sons, Inc., N.Y., incorporated herein by reference). Suitable promoters include but are not limited to LTR or SV40 promoter, E. coli lac, tac or trp promoters and the phage lambda P$_L$ promoter. Vectors will preferably incorporate an origin of replication as well as selection markers, i.e. antibiotic resistance gene. Suitable bacterial vectors include pET, pQE70, pQE60, pQE-9, pD10 phagescript, PSIX174, pBluescript SK, pbsks, pNH8A, pNH16A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial (i.e. *E. coli, Bacillus subtilis, Streptomyces*), fungial (i.e. *Aspergillus niger, Aspergillus nidulins*), yeast (i.e. *Saccharomyces*) or eukaryotic (i.e. CHO, COS).

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide.e. using ammonium sulfate or ethanol precipitation, acid extraction, anion or cation exchange chromatography, phosphocellulose chromatography hydrophobic interaction chromatography, hydroxylapatite chromatography and lectin chromatography. Final purification may be achieved using HPLC.

The polypeptide may be expressed with or without a leader or secretion sequence. In the former case, the leader may be removed using post-translational processing (see U.S. Pat. No. 4,431,739, U.S. Pat. No. 4,425,437 and U.S. Pat. No. 4,338,397 incorporated herein by reference) or be chemically removed subsequent to purifying the expressed polypeptide.

According to a further aspect, the GBS polypeptides of the invention may be used in a diagnostic test for GBS infection, in particular for GBS infection. Several diagnostic methods are possible, for example detecting GBS organism in a biological sample, the following procedure may be followed:

a. obtaining a biological sample from an individual;
b. incubating an antibody or fragment thereof reactive with an GBS polypeptide of the invention with the biological sample to form a mixture, and
c. detecting specifically bound antibody or bound fragment in the mixture which indicates the presence of GBS.

Alternatively, a method for the detection of antibody specific to a GBS antigen in a biological sample containing or suspected of containing said antibody may be performed as follows:

a. obtaining a biological sample from an individual;
b. incubating one or more GBS polypeptides of the invention or fragments thereof with the biological sample to form a mixture; and
c. detecting specifically bound antigen or bound fragment in the mixture which indicates the presence of antibody specific to GBS.

One of skill in the art will recognize that this diagnostic test may take several forms, including an immunological test such as an enzyme-linked immunoadsorbent assay (ELISA), a radioimmunoassay or a latex agglutination assay, essentially to determine whether antibodies specific for the polypeptide are present in an organism.

The polynucleotides encoding polypeptides of the invention may also be used to design DNA probes for use in detecting the presence of GBS in a biological sample suspected of containing such bacteria. The detection method of this invention comprises:

a. obtaining the biological sample from an individual;
b. incubating one or more DNA probes having a DNA sequence encoding a polypeptide of the invention or fragments thereof with the biological sample to form a mixture; and
c. detecting specifically bound DNA probe in the mixture which indicates the presence of GBS bacteria.

The DNA probes of this invention may also be used for detecting circulating GBS (i.e. GBS nucleic acids) in a sample, for example using a polymerase chain reaction, as a method of diagnosing GBS infections. The probe may be synthesized using conventional techniques and may be immobilized on a solid phase or may be labelled with a detectable label. A preferred DNA probe for this application is an oligomer having a sequence complementary to at least about 6 contiguous nucleotides of the GBS polypeptides of the invention.

Another diagnostic method for the detection of GBS in an individual comprises:
a. labelling an antibody reactive with a polypeptide of the invention or fragment thereof with a detectable label;
b. administering the labelled antibody or labelled fragment to the individual; and
c. detecting specifically bound labelled antibody or labelled fragment in the individual which indicates the presence of GBS.

A further aspect of the invention is the use of the GBS polypeptides of the invention as immunogens for the production of specific antibodies for the diagnosis and in particular the treatment of GBS infection. Suitable antibodies may be determined using appropriate screening methods, for example by measuring the ability of a particular antibody to passively protect against GBS infection in a test model. One example of an animal model is the mouse model described in the example herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal or preferably monoclonal. It may be specific for a number of epitopes associated with the GBS polypeptides but is preferably specific for one.

A further aspect of the invention is the use of a pharmaceutical composition of the invention for the prophylactic or therapeutic treatment of GBS infection comprising administering to said individual a prophylactic or therapeutic amount of the composition.

Unless otherwise defined, all technical and scientific terms used herein have the same meaning as commonly understood by one of ordinary skill in the art to which this invention belong. All publications, patent applications, patents and other references mentioned herein are incorporated by reference in their entirety. In case of conflict, the present specification including definitions, will control. In addition, the materials, methods, and examples are illustrative only and not intended to be limiting.

EXAMPLE 1

This example illustrates the identification of GBS BVH-A2 and BVH-A3 genes.

Chromosomal DNA was isolated from different GBS strains as previously described (Jayarao B M et al. 1991. J. Clin. Microbiol. 29:2774-2778). A λZAPExpress genomic library was constructed using chromosomal DNA purified from the serotype III GBS strain NCS954 and screened according to the manufacturer's instruction (Stratagene, La Jolla, Calif.) with a pool of human normal sera. Briefly, the purified chromosomal DNA was partially digested with tsp509I restriction enzyme, and the resulting fragments were electrophoresed on a 1% agarose gel (Bio-Rad). Fragments in the 5- to 10-kb size range were extracted from the gel and ligated to the EcoRI arms of λZAPExpress vector and the vector was encapsidated using the Gigapack II packaging extract (Stratagene). The recombinant phages were used to infect E. coli XL1-Blue MRF'[Δ(mcrA)183Δ(mcrCB-hsdSMR-mrr)173 endA1 supE44 thi-1 recA1 gyrA96 relA1 lac (F' proAB lacl$^q$ZΔM15 Tn10 [Tet$^R$])], which was then plated onto LB agar. The resulting plaques were lifted onto Hybond-C nitrocellulose membranes (Amersham Pharmacia Biotech, Baie d'Urfée, Canada) pre-impregnated with 10 mM Isopropyl-β-d-thiogalactopyranoside (IPTG: ICN Biomedicals Inc., Costa Mesa, Calif.). The membranes were blocked using phosphate-buffered saline (PBS) with 3% skim milk and were sequentially incubated with the pooled of human sera, peroxydase-labeled goat anti-human immunoglobulins antisera (Jackson Immunoresearch Laboratories Inc., West Grove, Pa.) and substrate. Positive plaques were isolated, purified twice, and the recombinant pBK-CMV plasmids (Stratagene) were excised with the ExAssist helper phage (Stratagene) according to the manufacturer's instructions. Immunoblots using phagemid vectors containing the cloned inserts revealed that the pooled human sera reacted with a protein band with an approximate molecular weight of 65 kDa for the clone H31-29, while it reacted with two protein bands with an approximate molecular weights between 40-60 kDa for the clone F8. These clones were respectively identified as BVH-A2 and BVH-A3. The sequence of the inserts were determined using the TAQ Dye Deoxy Terminator Cycle Sequencing Kit with an Applied Biosystems Inc. (Foster City, Calif.) automated sequencer model 373A according to the manufacturer's recommendations.

EXAMPLE 2

This example illustrates the cloning of GBS BVH-A2 and BVH-A3 genes.

The coding regions of Group B streptococcal BVH-A2 (SEQ ID NO: 1) and BVH-A3 (SEQ ID NO: 5) genes were respectively amplified by PCR (DNA Thermal Cycler Gene-Amp PCR system 2400 Perkin Elmer, San Jose, Calif.) from purified recombinant phagemid clone H31-29 and genomic DNA of serotype III Group[1'] B streptococcal strain NCS954 using oligonucleotide primers that contained base extensions for the addition of restriction sites NdeI (CATATG) and XhoI (CTCGAG). The oligonucleotide primers (Table 1) DMAR172 (SEQ ID No:9) and DMAR173 (SEQ ID No:10) were used to amplify the BVH-A2 gene, while DMAR204 (SEQ ID No:15) and DMAR205 (SEQ ID No:16) were used to amplify the BVH-A3 gene. PCR products were purified from agarose gel using a QIAquick gel extraction kit from QIAgen following the manufacturer's instructions (Chatsworth, Calif.), and digested with NdeI and XhoI (Pharmacia Canada Inc, Baie d'Urfé, Canada). The pET-21b(+) vector (Novagen, Madison, Wis.) was digested with NdeI and XhoI and purified from agarose gel using a QIAquick gel extraction kit from QIAgen (Chatsworth, Calif.). The NdeI-XhoI PCR products were ligated to the NdeI-XhoI pET-21b(+)expression vector. The ligated products were transformed into E. coli strain DH5α [φ80dlacZΔM15 Δ(lacZYA-argF)U169 endA1 recA1 hsdR17($r_K^-$–$m_K^-$+) deoR thi-1 supE44 λ$^-$gyrA96 relA1] (Gibco BRL, Gaithersburg, Md.) according to the method of Simanis (Hanahan, D. DNA Cloning, 1985, D. M. Glover (ed), pp. 109-135). Recombinant pET-21b(+)plasmids (rpET21b(+)) containing BVH-A2 or BVH-A3 genes were purified using a QIAgen plasmid kit (Chatsworth, Calif.) and DNA inserts were sequenced (Taq Dye Deoxy Terminator Cycle Sequencing kit, ABI, Foster City, Calif.).

It was determined that the open reading frame (ORF) which codes for BVH-A2 gene (SEQ ID NO: 1) contains 1626-bp and encodes a 541 amino acid residues polypeptide with a predicted pI of 8.99 and a predicted molecular mass of 59730.66 Da. Analysis of the predicted amino acid residues sequence (SEQ ID NO:3)using the Spscan software (Wisconsin Sequence Analysis Package; Genetics Computer Group) suggested the existence of a 37 amino acid residues signal peptide (MRGSLSTKQSYSLRKYKFGLASVILGS-FIMVTSPVFA), which end with a cleavage site situated between an alanine and a aspartic acid residues. Analysis of this ORP did not revealed the presence of repetitive structures, or IgA binding motif (MLKKIE), but a putative cell wall anchoring motif (LPKTG) was identified near the C-terminal end between amino acid residues 479 and 483. Comparison of the amino acid sequence of BVH-A2 (SEQ ID NO.3)with the sequences compiled in the available databanks revealed 18% identity with an hypothetical 40 kDa transmembrane exported protein of *Streptococcus mutans* which was located upstream the sr gene encoding the SR protein implicated in the interactions of *S. mutans* with salivary glycoproteins (GeneBank accession number: c60328: Ogier et al 1991. Infection and Immunity.59:1620-1626).

Computer Group) suggested the existence of a 28 amino acid residues signal peptide (MKIKKIISGFAAALIISSL-STINYEVKA), which ends with a cleavage site situated between an alanine and an aspartic acid residues. Analysis of this ORF did not revealed the presence of repetitive structures, cell wall anchoring motif (LPXTG), or IgA binding motif (MLKKIE). Comparison of the amino acid sequence of BVH-A3 (SEQ ID NO.7) with the sequences compiled in the available databanks did not reveal any significant homology with sequences available in the databanks.

EXAMPLE 3

This example describes the PCR amplification of GBS BVH-A2 and BVH-A3 genes from other GBS strains To confirm the presence by PCR amplification of BVH-A2 (SEQ ID NO:1) and BVH-A3 (SEQ ID NO:5) genes, the following 11 serologically distinct GBS strains were used: C388/90 (serotype Ia/c), ATCC12401 (serotype Ib), ATCC27591 (serotype Ic), NCS246 (serotype II/R), NCS954 (serotype III), NCS97SR331 (serotype IV), NCS535 (serotype V), NCS9842 (serotype VI), NCS7271 (serotype VII), NCS970886 (serotype VIII), ATCC27956 (bovine isolate). These strains were obtained from the American Type Culture Collection (Rockville, Md., USA) and National Centre for *Streptococcus*, Provincial Labora-

TABLE 1

Oligonucleotide primers used for PCR amplifications of GBS BVH-A2 and BVH-A3 genes

| Genes | Oligonucleotide primers I.D. | Sequences |
|---|---|---|
| BVH-A2 | DMAR172 (SEQ ID No 9) | 5'-CTTTGGGGAACATATGAGGGGATCTC-3' |
| BVH-A2 | DMAR173 (SEQ ID No 10) | 5'-CTAAAAAGATTTACTCGAGAATTTCAATATAGCG-3' |
| BVH-A2 | DMAR373 (SEQ ID No 11) | 5'-ATGAGGGGATCTCTCAGTACTAAGCAATCTT-3' |
| BVH-A2 | DMAR374 (SEQ ID No 12) | 5'-TTAAATTTCAATATAGCGACGAATACCGGA-3' |
| BVH-A2 | DMAR464 (SEQ ID No 13) | 5'-CATAGGATCCGGATCAAACTACATCGGTTCAAG-3' |
| BVH-A2 | DMAR465 (SEQ ID No 14) | 5'-CCGGGTCGACTTAAATTTCAATATAGCGACG-3' |
| BVH-A3 | DMAR204 (SEQ ID No 15) | 5'-CACAGGAGAACATATGAAGATTAAAAAAATTATTAGTGGCTTTGCC-3' |
| BVH-A3 | DMAR205 (SEQ ID No 16) | 5'-CTTTCTCGAGTGCACCTTGATGGCGATCAGC-3' |
| BVH-A3 | DMAR466 (SEQ ID No 17) | 5'-CATAGGATCCTGATGACACCACCAGTGAGTATCACTATATC-3' |
| BVH-A3 | DMAR467 (SEQ ID No 18) | 5'-CATAGTCGACTTATGCACCTTGATGGCGATCAG-3' |

It was determined that the open reading frame (ORF) which codes for BVH-A3 gene (SEQ ID NO:5) contains 1590-bp and encodes a 529 amino acid residues polypeptide with a predicted pI of 6.14 and a predicted molecular mass of 59019.48 Da. Analysis of the predicted amino acid residues sequence (SEQ ID NO:7) using the Spscan software (Wisconsin Sequence Analysis Package; Genetics tory of Public Health for Northern Alberta (Edmonton, Canada). The *E. coli* strain XL1-Blue MRF' was used in these experiments as negative control. Chromosomal DNA was isolated from each Group B streptococcal strain as previously described (Jayarao BM et al. 1991. J. Clin. Microbiol. 29:2774-2778). BVH-A2 (SEQ ID NO:1) and BVH-A3 (SEQ ID NO:5) genes were amplified by PCR (DNA Thermal Cycler GeneAmp PCR system 2400 Perkin Elmer, San Jose, Calif.) from the genomic DNA purified from the 11 GBS strains, and the control *E. coli* strain using the oligonucleotides presented in Table 1. The oligonucleotide primers DMAR373 (SEQ ID No:11) and DMAR374 (SEQ ID No:12) were used to amplify the BVH-A2 (SEQ ID NO:1) gene, while DMAR204 (SEQ ID No:15) and DMAR205 (SEQ ID No:16) were used to amplify the BVH-A3 (SEQ ID NO:5) gene. PCR was performed with 35 cycles of 45 sec at 94° C., 45 sec at 55° C. and 2 min at 72° C. and a final elongation period of 10 min at 72° C. The PCR products were size fractionated in 1% agarose gels and were visualized by ethidium bromide staining. The results of these PCR amplifications are presented in Table 2. The analysis of the amplification products revealed that both BVH-A2 (SEQ ID NO:1) and BVH-A3 (SEQ ID NO:5) genes were present in the genome of all of the 11 GBS strains tested. No such product was detected when the control *E. coli* DNA was submitted to identical PCR amplifications with both sets of oligonucleotide primers.

TABLE 2

Identification of BVH-A2 and BVH-A3 genes by PCR amplification

| Strains identification | Identification by PCR amplification of | |
|---|---|---|
| GBS isolates | BVH-A2 | BVH-A3 |
| C388/90 (serotype Ia/c) | + | + |
| ATCC12401 (serotype Ib) | + | + |
| ATCC27591 (serotype Ic) | + | + |
| NCS246 (serotype II/R) | + | + |
| NCS954 (serotype III) | + | + |
| NCS97SR331 (serotype IV) | + | + |
| NCS535 (serotype V) | + | + |
| NCS9842 (serotype VI) | + | + |
| NCS7271 (serotype VII) | + | + |
| NCS970886 (serotype VIII) | + | + |
| ATCC27956 (bovine isolate) | + | + |
| *E. coli* control strain XL1 Blue MRF' | − | − |

EXAMPLE 4

This example illustrates the cloning of GBS BVH-A2 and BVH-A3 genes in CMV plasmid PCMV-GH.

The DNA coding region of Group B streptococcal BHV-A2 (SEQ ID NO:4) and BVH-A3 (SEQ ID NO:8) polypeptides were inserted in phase downstream of a human growth hormone (hGH) gene which was under the transcriptional control of the cytomegalovirus (CMV) promotor in the plasmid vector pCMV-GH (Tang et al., Nature, 1992, 356: 152). The CMV promotor is non functional plasmid in *E. coli* cells but active upon administration of the plasmid in eukaryotic cells. The vector also incorporated the ampicillin resistance gene.

The coding regions of BVH-A2 (SEQ ID NO: 2) and BVH-A3 (SEQ ID NO: 6) genes without their leader peptide regions were amplified by PCR (DNA Thermal Cycler GeneAmp PCR system 2400 Perkin Elmer, San Jose, Calif.) from genomic DNA of serotype III GBS strain NCS954 using oligonucleotide primers that contained base extensions for the addition of restriction sites BamHI (GGATCC) and SalI (GTCGAC). The oligonucletide primers DMAR464 (SEQ ID No:13) and DMAR465 (SEQ ID No:14) were used to amplify the BVH-A2 (SEQ ID NO:2) gene, while DMAR466 (SEQ ID No:17) and DMAR467 (SEQ ID No:18) were used to amplify the BVH-A3 (SEQ ID NO:6) genes. The PCR products were purified from agarose gel using a QIAquick gel extraction kit from QIAgen (Chatsworth, Calif.), digested with restriction enzymes (Pharmacia Canada Inc, Baie d'Urfe, Canada). The pCMV-GH vector (Laboratory of Dr. Stephen A. Johnston, Department of Biochemistry, The University of Texas, Dallas, Tex.) was digested with BamHI and SalI and purified from agarose gel using the QIAquick gel extraction kit from QIAgen (Chatsworth, Calif.). The BamHI-SalI DNA fragments were ligated to the BamHI-SalI pCMV-GH vector to create the hGH-BVH-A2 and hGH-BVH-A3 fusion polypeptides under the control of the CMV promoter. The ligated products were transformed into *E. coli* strain DH5α [φ80dlacZΔM15 Δ(lacZYA-argF)U169 endA1 recA1 hsdR17($r_K^-$–$m_K^+$) deoR thi-1 supE44 λ$^-$gyrA96 relA1] (Gibco BRL, Gaithersburg, Md.) according to the method of Simanis (Hanahan, D. DNA Cloning, 1985, D. M. Glover (ed), pp. 109-135). The recombinant pCMV plasmids were purified using a QIAgen plasmid kit (Chatsworth, Calif.) and the nucleotide sequences of the DNA inserts were verified by DNA sequencing.

EXAMPLE 5

This example illustrates the use of DNA to elicit an immune response to GBS BVH-A2 and BVH-A3 polypeptide antigens.

Groups of 8 female BALB/c mice (Charles River, St-Constant, Québec, Canada) are immunized by intramuscular injection of 100 μl three times at two- or three-week intervals with 50 μg of recombinant pCMV-GH encoding BVH-A2 (SEQ ID NO:2) or BVH-A3 (SEQ ID NO:6) genes in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, groups of mice are injected with 50 μg of pCMV-GH in presence of 50 μg of pCMV-GH-GM-CSF. Blood samples are collected from the orbital sinus prior to each immunization and seven days following the third injection and serum antibody responses are determined by ELISA using either purified BVH-A2-His.Tag or BVH-A3-His.Tag recombinant polypeptides as coating antigens.

EXAMPLE 6

This example illustrates the production and purification of recombinant GBS BVH-A2 and BVH-A3 polypeptides.

The recombinant pET-21b(+)plasmids with BVH-A2 or BVH-A3 genes respectively corresponding to the SEQ ID NO: 1, and SEQ ID NO: 5 are used to transform by electroporation (Gene Pulser II apparatus, BIO-RAD Labs, Mississauga, Canada) *E. coli* strain BL21(DE3) (F$^-$ompT hsdS$_\beta$ ($r^-_B m^-_B$) gal dcm (DE3)) (Novagen, Madison, Wis.). In this strain of *E. coli*, the T7 promotor controlling expression of the recombinant polypeptide is specifically recognized by the T7 RNA polymerase (present on the λDE3 prophage) whose gene is under the control of the lac promotor which is inducible by isopropyl-β-d-thio-galactopyranoside (IPTG). The transformants BL21(DE3)/rpET are grown at 37° C. with agitation at 250 rpm in LB broth (peptone 10 g/L, yeast extract 5 g/L, NaCl 10 g/L) containing 100 µg of carbenicillin (Sigma-Aldrich Canada Ltd., Oakville, Canada) per mL until the $A_{600}$ reaches a value of 0.6. In order to induce the production of GBS BVH-A2-His.Tag and BVH-A3-His.Tag recombinant polypeptides, the cells are incubated for 3 additional hours in the presence of IPTG at a final concentration of 1 mM. Induced cells from a 500 ml culture are pelleted by centrifugation and frozen at −70° C.

The purification of the recombinant polypeptides from the soluble cytoplasmic fraction of IPTG-induced BL21(DE3)/rpET21b(+) is done by affinity chromatography based on the properties of the His.Tag sequence (6 consecutive histidine residues) to bind to divalent cations ($Ni^{2+}$) immobilized on the His.Bind metal chelation resin. Briefly, the pelleted cells obtained from a 500 mL culture induced with IPTG are resuspended in lysis buffer (20 mM Tris, 500 mM NaCl, 10 mM imidazole, pH 7.9) containing 1 mM PMSF, sonicated and centrifuged at 12,000×g for 20 min to remove debris. The supernatant is deposited on a Ni-NTA agarose column (Qiagen, Mississauga, Ontario, Canada). The GBS BVH-A2-His.Tag and BVH-A3-His.Tag recombinant polypeptides are eluted with 250 mM imidazole-500 mM NaCl-20 mM Tris pH 7.9. The removal of the salt and imidazole from the samples is done by dialysis against PBS at 40° C. The quantities of recombinant polypeptides obtained from the soluble fraction of *E. coli* are estimated by MicroBCA (Pierce, Rockford, Ill.).

EXAMPLE 7

This example illustrates the accessibility to antibodies of the GBS BVH-A2 and BVH-A3 polypeptides at the surface of GBS strains.

Bacteria are grown in Todd Hewitt (TH) broth (Difco Laboratories, Detroit Mich.) with 0.5% Yeast extract (Difco Laboratories) and 0.5% peptone extract (Merck, Darmstadt, Germany) at 37° C. in a 8% $CO_2$ atmosphere to give an $OD_{490}$ nm of 0.600 (~$10^8$ CFU/ml). Dilutions of anti-BVH-A2, anti-BVH-A3 or control sera are then added and allowed to bind to the cells, which are incubated for 2 h at 4° C. Samples are washed 4 times in blocking buffer [phosphate-buffered saline (PBS) containing 2% bovine serum albumin (BSA)], and then 1 mL of goat fluorescein (FITC)-conjugated anti-mouse IgG+IgM diluted in blocking buffer is added. After an additional incubation of 60 min at room temperature, samples are washed 4 times in blocking buffer and fixed with 0.25% formaldehyde in PBS buffer for 18-24 h at 4° C. Cells are washed 2 times in PBS buffer and resuspended in 500 µl of PBS buffer. Cells are kept in the dark at 4° C. until analyzed by flow cytometry (Epics® XL; Beckman Coulter, Inc.).

EXAMPLE 8

This example illustrates the protection against fatal GBS infection induced by passive immunization of mice with rabbit hyper-immune sera.

New Zealand rabbits (Charles River laboratories, St-Constant, Canada) are injected subcutaneously at multiple sites with 50 µg and 100 µg of BVH-A2-His.Tag or BVH-A3-His.Tag polypeptides that are produced and purified as described in Example 6 and adsorbed to Alhydrogel adjuvant (Superfos Biosector a/s). Rabbits are immunized three times at three-week intervals with the BVH-A2-His.Tag or BVH-A3-His.Tag polypeptides. Blood samples are collected three weeks after the third injection. The antibodies present in the serum are purified by precipitation using 40% saturated ammonium sulfate. Groups of 10 female CD-1 mice (Charles River) are injected intravenously with 500 µl of purified serum collected either from BVH-A2-His.Tag, or BVH-A3-His.Tag immunized rabbits, or rabbits immunized with an unrelated control recombinant protein. Eighteen hours later the mice are challenged with approximately $8×10^4$ CFU of the GBS strain C388/90 (Ia/c). Samples of the GBS challenge inoculum are plated on blood agar plates to determine the CFU and to verify the challenge dose. Deaths are recorded for a period of 14 days.

EXAMPLE 9

This example illustrates the protection of mice against fatal GBS infection induced by immunization.

Groups of 8 female CD-1 mice (Charles River) are immunized subcutaneously three times at three-week intervals with 20 µg of either BVH-A2-His.Tag or BVH-A3-His.Tag polypeptides that are produced and purified as described in Example 6 in presence of 10 µg of QuilA adjuvant (Cedarlane Laboratories Ltd, Hornby, Canada). The control mice are injected with QuilA adjuvant alone in PBS. Blood samples are collected from the orbital sinus on day 1, 22 and 43 prior to each immunization and seven days (day 50) following the third injection. Two weeks later the mice are challenged with approximately $8×10^4$ CPU of the GBS strain C388/90 (Ia/c). Samples of the GBS challenge inoculum are plated on blood agar plates to determine the CFU and to verify the challenge dose. Deaths are recorded for a period of 14 days.

What is claimed is:

1. An isolated polypeptide comprising
an amino acid sequence at least 95% identical to the amino acid sequence set forth in either SEQ ID NO:7 or SEQ ID NO:8,
wherein the isolated polypeptide is capable of raising antibodies that specifically bind to a polypeptide comprising the amino acid sequence set forth in either SEQ ID NO:7 or SEQ ID NO:8.

2. An isolated polypeptide comprising:
(a) the amino acid sequence set forth in SEQ ID NO:7;
(b) the amino acid sequence set forth in SEQ ID NO: 8;
(c) the polypeptide of (a), wherein the N-terminal methionine residue is deleted; or
(d) the polypeptide of (a), wherein the signal peptide amino acid sequence is deleted.

3. A chimeric polypeptide comprising two or more polypeptides wherein each of the two or more polypeptides comprises at least twenty contiguous amino acids of the amino acid set forth in SEQ ID NO:8, and wherein the two or more polypeptides are linked as to form a chimeric polypeptide.

4. A chimeric polypeptide comprising two or more polypeptides wherein each of the two or more polypeptides comprises a sequence chosen from SEQ ID NOS: 7 and 8, and wherein the two or more polypeptides are linked as to form a chimeric polypeptide.

5. A pharmaceutical composition comprising a polypeptide according to claim 1 or claim 2 and a pharmaceutically acceptable carrier, diluent or adjuvant.

6. A kit comprising the polypeptide according to either claim 1 or claim 2 for detection or diagnosis of a group B *Streptococcus* infection.

7. An isolated polypeptide comprising a fragment that comprises at least twenty contiguous amino acids of the amino acid sequence set forth in SEQ ID NO:8,
wherein the isolated polypeptide is capable of raising antibodies that specifically bind to a polypeptide comprising the amino acid sequence set forth in either SEQ ID NO:7 or SEQ ID NO:8.

8. A pharmaceutical composition comprising the polypeptide according to claim 7 and a pharmaceutically acceptable carrier, diluent, or adjuvant.

* * * * *

SEQUENCE LISTING

<160> NUMBER OF SEQ ID NOS: 21

<210> SEQ ID NO 1
<211> LENGTH: 1626
<212> TYPE: DNA
<213> ORGANISM: Group B Streptococcus

<400> SEQUENCE: 1
atgaggggat ctctcagtac taagcaatct tactctctac gtaaatataa atttggttta     60

```
gcatcagtaa ttttagggtc attcataatg gtcacaagtc ctgttttgc ggatcaaact       120 acatcggttc aagttaataa tcagacaggc actagtgtgg atgctaataa ttcttccaat      180
gagacaagtg cgtcaagtgt gattacttcc aataatgata gtgttcaagc gtctgataaa      240
gttgtaaata gtcaaaatac ggcaacaaag gacattacta ctcctttagt agagacaaag      300
ccaatggtgg aaaaaacatt acctgaacaa gggaattatg tttatagcaa agaaaccgag      360
gtgaaaaata caccttcaaa atcagcccca gtagctttct atgcaaagaa aggtgataaa      420
gttttctatg accaagtatt taataaagat aatgtgaaat ggatttcata taagtctttt      480
ggtggcgtac gtcgatacgc agctattgag tcactagatc catcaggagg ttcagagact      540
aaagcaccta ctcctgtaac aaattcagga agcaataatc aagagaaaat agcaacgcaa      600
ggaaattata cattttcaca taagtagaa gtaaaaaatg aagctaaggt agcgagtcca       660
actcaattta cattggacaa aggagacaga atttttttacg accaaatact aactattgaa      720
ggaaatcagt ggttatctta taaatcattc aatggtgttc gtcgttttgt tttgctaggt      780
aaagcatctt cagtagaaaa aactgaagat aaagaaaaag tgtctcctca accacaagcc      840
cgtattacta aaactggtag actgactatt tctaacgaaa caactacagg ttttgatatt      900
ttaattacga atattaaaga tgataacggt atcgctgctg ttaaggtacc ggtttggact      960
gaacaaggag ggcaagatga tattaaatgg tatacagctg taactactgg ggatggcaac     1020
tacaaagtag ctgtatcatt tgctgaccat aagaatgaga agggtcttta taatattcat     1080
ttatactacc aagaagctag tgggacactt gtaggtgtaa caggaactaa agtgacagta     1140
gctggaacta attcttctca agaacctatt gaaaatggtt taccaaagac tggtgtttat     1200
aatattatcg gaagtactga gtaaaaaaat gaagctaaaa tatcaagtca gacccaattt     1260
actttagaaa aaggtgacaa aataaattat gatcaagtat tgacagcaga tggttaccag     1320
tggatttctt acaaatctta tagtggtgtt cgtcgctata ttcctgtgaa aaagctaact     1380
acaagtagtg aaaaagcgaa agatgaggcg actaaaccga ctagttatcc caacttacct     1440
aaaacaggta cctatacatt tactaaaact gtagatgtga aaagtcaacc taaagtatca     1500
agtccagtgg aatttaattt tcaaaagggt gaaaaaatac attatgatca agtgttagta     1560
gtagatggtc atcagtggat ttcatacaag agttattccg gtattcgtcg ctatattgaa     1620
atttaa                                                               1626
```

<210> SEQ ID NO 2
<211> LENGTH: 1515
<212> TYPE: DNA
<213> ORGANISM: Group B Streptococcus

<400> SEQUENCE: 2

```
gatcaaacta catcggttca agttaataat cagacaggca ctagtgtgga tgctaataat       60
tcttccaatg agacaagtgc gtcaagtgtg attacttcca ataatgatag tgttcaagcg      120
tctgataaag ttgtaaatag tcaaaatacg gcaacaaagg acattactac tcctttagta      180
gagacaaagc caatggtgga aaaaacatta cctgaacaag ggaattatgt ttatagcaaa      240
gaaaccgagg tgaaaaatac accttcaaaa tcagcccag tagctttcta tgcaaagaaa      300
ggtgataaag ttttctatga ccaagtattt aataaagata atgtgaaatg gatttcatat      360
aagtcttttg gtggcgtacg tcgatacgca gctattgagt cactagatcc atcaggaggt      420
tcagagacta aagcacctac tcctgtaaca aattcaggaa gcaataatca agagaaaata      480
gcaacgcaag gaaattatac attttcacat aagtagaag taaaaaatga agctaaggta      540
```

-continued

```
gcgagtccaa ctcaatttac attggacaaa ggagacagaa ttttttacga ccaaatacta    600
actattgaag gaaatcagtg gttatcttat aaatcattca atggtgttcg tcgtttttgtt   660 ttgctaggta agcatcttc agtagaaaaa actgaagata agaaaaagt gtctcctcaa      720 ccacaagccc gtattactaa actggtaga ctgactattt ctaacgaaac aactacaggt     780
tttgatattt taattacgaa tattaaagat gataacggta tcgctgctgt taaggtaccg    840
gtttggactg aacaaggagg gcaagatgat attaaatggt atacagctgt aactactggg    900
gatggcaact acaaagtagc tgtatcattt gctgaccata agaatgagaa gggtctttat    960
aatattcatt tatactacca agaagctagt gggacacttg taggtgtaac aggaactaaa   1020
gtgacagtag ctggaactaa ttcttctcaa gaacctattg aaaatggttt accaaagact   1080
ggtgtttata atattatcgg aagtactgaa gtaaaaaatg aagctaaaat atcaagtcag   1140
acccaattta ctttagaaaa aggtgacaaa ataaattatg atcaagtatt gacagcagat   1200
ggttaccagt ggatttctta caaatcttat agtggtgttc gtcgctatat tcctgtgaaa   1260
aagctaacta caagtagtga aaaagcgaaa gatgaggcga ctaaaccgac tagttatccc   1320
aacttaccta aaacaggtac ctatacattt actaaaactg tagatgtgaa aagtcaacct   1380
aaagtatcaa gtccagtgga atttaatttt caaaagggtg aaaaaaataca ttatgatcaa   1440 gtgttagtag tagatggtca tcagtggatt tcatacaaga gttattccgg tattcgtcgc   1500
tatattgaaa tttaa                                                    1515
```

<210> SEQ ID NO 3
<211> LENGTH: 541
<212> TYPE: PRT
<213> ORGANISM: Group B Streptococcus

<400> SEQUENCE: 3

```
Met Arg Gly Ser Leu Ser Thr Lys Gln Ser Tyr Ser Leu Arg Lys Tyr
 1               5                  10                  15

Lys Phe Gly Leu Ala Ser Val Ile Leu Gly Ser Phe Ile Met Val Thr
            20                  25                  30

Ser Pro Val Phe Ala Asp Gln Thr Thr Ser Val Gln Val Asn Asn Gln
        35                  40                  45

Thr Gly Thr Ser Val Asp Ala Asn Asn Ser Ser Asn Glu Thr Ser Ala
    50                  55                  60

Ser Ser Val Ile Thr Ser Asn Asn Asp Ser Val Gln Ala Ser Asp Lys
65                  70                  75                  80

Val Val Asn Ser Gln Asn Thr Ala Thr Lys Asp Ile Thr Thr Pro Leu
                85                  90                  95

Val Glu Thr Lys Pro Met Val Glu Lys Thr Leu Pro Glu Gln Gly Asn
            100                 105                 110

Tyr Val Tyr Ser Lys Glu Thr Glu Val Lys Asn Thr Pro Ser Lys Ser
        115                 120                 125

Ala Pro Val Ala Phe Tyr Ala Lys Lys Gly Asp Lys Val Phe Tyr Asp
    130                 135                 140

Gln Val Phe Asn Lys Asp Asn Val Lys Trp Ile Ser Tyr Lys Ser Phe
145                 150                 155                 160

Gly Gly Val Arg Arg Tyr Ala Ala Ile Glu Ser Leu Asp Pro Ser Gly
                165                 170                 175

Gly Ser Glu Thr Lys Ala Pro Thr Pro Val Thr Asn Ser Gly Ser Asn
            180                 185                 190
```

```
Asn Gln Glu Lys Ile Ala Thr Gln Gly Asn Tyr Thr Phe Ser His Lys
            195                 200                 205

Val Glu Val Lys Asn Glu Ala Lys Val Ala Ser Pro Thr Gln Phe Thr
        210                 215                 220

Leu Asp Lys Gly Asp Arg Ile Phe Tyr Asp Gln Ile Leu Thr Ile Glu
225                 230                 235                 240

Gly Asn Gln Trp Leu Ser Tyr Lys Ser Phe Asn Gly Val Arg Arg Phe
                245                 250                 255

Val Leu Leu Gly Lys Ala Ser Ser Val Glu Lys Thr Glu Asp Lys Glu
            260                 265                 270

Lys Val Ser Pro Gln Pro Gln Ala Arg Ile Thr Lys Thr Gly Arg Leu
        275                 280                 285

Thr Ile Ser Asn Glu Thr Thr Thr Gly Phe Asp Ile Leu Ile Thr Asn
290                 295                 300

Ile Lys Asp Asp Asn Gly Ile Ala Ala Val Lys Val Pro Val Trp Thr
305                 310                 315                 320

Glu Gln Gly Gly Gln Asp Ile Lys Trp Tyr Thr Ala Val Thr Thr
                325                 330                 335

Gly Asp Gly Asn Tyr Lys Val Ala Val Ser Phe Ala Asp His Lys Asn
                340                 345                 350

Glu Lys Gly Leu Tyr Asn Ile His Leu Tyr Tyr Gln Glu Ala Ser Gly
            355                 360                 365

Thr Leu Val Gly Val Thr Gly Thr Lys Val Thr Val Ala Gly Thr Asn
        370                 375                 380

Ser Ser Gln Glu Pro Ile Glu Asn Gly Leu Pro Lys Thr Gly Val Tyr
385                 390                 395                 400

Asn Ile Ile Gly Ser Thr Glu Val Lys Asn Glu Ala Lys Ile Ser Ser
                405                 410                 415

Gln Thr Gln Phe Thr Leu Glu Lys Gly Asp Lys Ile Asn Tyr Asp Gln
            420                 425                 430

Val Leu Thr Ala Asp Gly Tyr Gln Trp Ile Ser Tyr Lys Ser Tyr Ser
        435                 440                 445

Gly Val Arg Arg Tyr Ile Pro Val Lys Lys Leu Thr Thr Ser Ser Glu
    450                 455                 460

Lys Ala Lys Asp Glu Ala Thr Lys Pro Thr Ser Tyr Pro Asn Leu Pro
465                 470                 475                 480

Lys Thr Gly Thr Tyr Thr Phe Thr Lys Thr Val Asp Val Lys Ser Gln
                485                 490                 495

Pro Lys Val Ser Ser Pro Val Glu Phe Asn Phe Gln Lys Gly Glu Lys
            500                 505                 510

Ile His Tyr Asp Gln Val Leu Val Asp Gly His Gln Trp Ile Ser
        515                 520                 525

Tyr Lys Ser Tyr Ser Gly Ile Arg Arg Tyr Ile Glu Ile
    530                 535                 540

<210> SEQ ID NO 4
<211> LENGTH: 504
<212> TYPE: PRT
<213> ORGANISM: Group B Streptococcus

<400> SEQUENCE: 4

Asp Gln Thr Thr Ser Val Gln Val Asn Asn Gln Thr Gly Thr Ser Val
1               5                   10                  15

Asp Ala Asn Asn Ser Ser Asn Glu Thr Ser Ala Ser Ser Val Ile Thr
            20                  25                  30
```

```
Ser Asn Asn Asp Ser Val Gln Ala Ser Asp Lys Val Val Asn Ser Gln
         35                  40                  45

Asn Thr Ala Thr Lys Asp Ile Thr Thr Pro Leu Val Glu Thr Lys Pro
 50                  55                  60

Met Val Glu Lys Thr Leu Pro Glu Gln Gly Asn Tyr Val Tyr Ser Lys
 65                  70                  75                  80

Glu Thr Glu Val Lys Asn Thr Pro Ser Lys Ser Ala Pro Val Ala Phe
                 85                  90                  95

Tyr Ala Lys Lys Gly Asp Lys Val Phe Tyr Asp Gln Val Phe Asn Lys
             100                 105                 110

Asp Asn Val Lys Trp Ile Ser Tyr Lys Ser Phe Gly Gly Val Arg Arg
         115                 120                 125

Tyr Ala Ala Ile Glu Ser Leu Asp Pro Ser Gly Gly Ser Glu Thr Lys
     130                 135                 140

Ala Pro Thr Pro Val Thr Asn Ser Gly Ser Asn Asn Gln Glu Lys Ile
145                 150                 155                 160

Ala Thr Gln Gly Asn Tyr Thr Phe Ser His Lys Val Glu Val Lys Asn
                165                 170                 175

Glu Ala Lys Val Ala Ser Pro Thr Gln Phe Thr Leu Asp Lys Gly Asp
            180                 185                 190

Arg Ile Phe Tyr Asp Gln Ile Leu Thr Ile Glu Gly Asn Gln Trp Leu
        195                 200                 205

Ser Tyr Lys Ser Phe Asn Gly Val Arg Arg Phe Val Leu Leu Gly Lys
    210                 215                 220

Ala Ser Ser Val Glu Lys Thr Glu Asp Lys Glu Lys Val Ser Pro Gln
225                 230                 235                 240

Pro Gln Ala Arg Ile Thr Lys Thr Gly Arg Leu Thr Ile Ser Asn Glu
                245                 250                 255

Thr Thr Thr Gly Phe Asp Ile Leu Ile Thr Asn Ile Lys Asp Asp Asn
            260                 265                 270

Gly Ile Ala Ala Val Lys Val Pro Val Trp Thr Glu Gln Gly Gly Gln
        275                 280                 285

Asp Asp Ile Lys Trp Tyr Thr Ala Val Thr Thr Gly Asp Gly Asn Tyr
    290                 295                 300

Lys Val Ala Val Ser Phe Ala Asp His Lys Asn Glu Lys Gly Leu Tyr
305                 310                 315                 320

Asn Ile His Leu Tyr Tyr Gln Glu Ala Ser Gly Thr Leu Val Gly Val
                325                 330                 335

Thr Gly Thr Lys Val Thr Val Ala Gly Thr Asn Ser Ser Gln Glu Pro
            340                 345                 350

Ile Glu Asn Gly Leu Pro Lys Thr Gly Val Tyr Asn Ile Ile Gly Ser
        355                 360                 365

Thr Glu Val Lys Asn Glu Ala Lys Ile Ser Ser Gln Thr Gln Phe Thr
    370                 375                 380

Leu Glu Lys Gly Asp Lys Ile Asn Tyr Asp Gln Val Leu Thr Ala Asp
385                 390                 395                 400

Gly Tyr Gln Trp Ile Ser Tyr Lys Ser Tyr Ser Gly Val Arg Arg Tyr
                405                 410                 415

Ile Pro Val Lys Lys Leu Thr Thr Ser Ser Glu Lys Ala Lys Asp Glu
            420                 425                 430

Ala Thr Lys Pro Thr Ser Tyr Pro Asn Leu Pro Lys Thr Gly Thr Tyr
        435                 440                 445
```

```
Thr Phe Thr Lys Thr Val Asp Val Lys Ser Gln Pro Lys Val Ser Ser
    450                 455                 460

Pro Val Glu Phe Asn Phe Gln Lys Gly Glu Lys Ile His Tyr Asp Gln
465                 470                 475                 480

Val Leu Val Val Asp Gly His Gln Trp Ile Ser Tyr Lys Ser Tyr Ser
                485                 490                 495

Gly Ile Arg Arg Tyr Ile Glu Ile
            500

<210> SEQ ID NO 5
<211> LENGTH: 1590
<212> TYPE: DNA
<213> ORGANISM: Group B Streptococcus

<400> SEQUENCE: 5
atgaagatta aaaaaattat tagtggcttt gccgcagctt taattatcag ttcactatca      60
actattaact atgaggttaa agctgatgac accaccagtg agtatcacta tatcagtaag     120
caaaataatg aaaagcagct tattagttac atcaaggaac aacatcgttt gctcaatcaa     180
tttgttgttg ataatgtcaa ctcattcact caactaaatg ctaatccaac tattgaacag     240
ttaaatagag ctataacatt atttaaacaa aaagatgagc aattatttaa ccaggtgaaa     300
gctggtcatc tctctcccag taactataat gctatcgtta atcaacgtaa tgtcattaac     360
caaactgttc aaaatctgat tgaccaaaat cataataaga ttcagacaag tcaaaataaa     420
gcagctcagc tcgtggggca acgtaatcag gttgttaaca aaattcaagc tattttagca     480 actgtaaaact acaactctgt gaattctata caagaagctg aaaatttatt tcattcactc     540
agaaatcaaa ttgaacctct tgtagctgaa gttaataatt acaaagctgc tatggcaatc     600
cttcaacaag aagtagatgc cctatcaaca gcggctattg aaactgagac ttctaaactt     660
gctactctca agttagcgaa aatacttct gttcctgcaa acaaagtaga agaaaaaact     720
actcaatcag aagcgtcagg caataaacaa gaagtaacta gagtgagga aaaacaggct     780 acctctgatg caaaggcatc acagcctgag tcagctaata ttgccgatta cgatagttta     840
aaagaagttt tacgaaataa tattagcaac caagtaccac acatcagtgt tcaaatggag     900
tttaaaactc aagaacaagt tgacgaatac caaaaaaatc tcggaagcat catccgggaa     960
attggagata cacttggaac agcaactgaa ttcaatgcca aaagtaacat tagcacttat    1020
actcttggtg acaaatcca acgcattatt gtaaaagcg acatcacaat cacctatact     1080
cttaaaggtg acatggtagg attacataaa gaatataaac agtttgtaga ttcttttgtc    1140
aaagaaaata ttactaacaa aaatatcaca agtgattatg aaaagctaa agtaattcat     1200 gaccacttgg ttaataatta cacttacgcg actgaagaac tggcaaccac tcgtgaaact    1260
gctagtggta tcagtatcca tgctcctgaa gcactctaca agataaacg tggtgttttgt     1320 caagcctttg cagtaatgtt taagatatg gctgctgctg gcttatcagt atggtatgta    1380
actggtcaag ctggaggtgg aaatcacgct tggaacattg ttactattaa tggcgttaaa    1440
tattatgttg atacaacatg ggataataat ataaaaagca ataaatattt ccttgttggt    1500
aaaacaataa tggatgctga tcatctttttg gatagtcaat acaatgcatt agctaaagat    1560
attccagctg atcgccatca aggtgcataa                                     1590

<210> SEQ ID NO 6
<211> LENGTH: 1506
<212> TYPE: DNA
<213> ORGANISM: Group B Streptococcus
```

<400> SEQUENCE: 6

```
gatgacacca ccagtgagta tcactatatc agtaagcaaa ataatgaaaa gcagcttatt      60
agttacatca aggaacaaca tcgtttgctc aatcaatttg ttgttgataa tgtcaactca     120
ttcactcaac taaatgctaa tccaactatt gaacagttaa atagagctat aacattattt     180
aaacaaaaag atgagcaatt atttaaccag gtgaaagctg gtcatctctc tcccagtaac     240
tataatgcta tcgttaatca acgtaatgtc attaaccaaa ctgttcaaaa tctgattgac     300
caaaatcata taagattca gacaagtcaa aataaagcag ctcagctcgt ggggcaacgt      360
aatcaggttg ttaacaaaat tcaagctatt ttagcaactg taaactacaa ctctgtgaat     420
tctatacaag aagctgaaaa ttttatttcat tcactcagaa atcaaattga acctcttgta    480
gctgaagtta ataattacaa agctgctatg gcaatccttc aacaagaagt agatgcccta     540
tcaacagcgg ctattgaaac tgagacttct aaacttgcta ctctcaaagt tagcgaaaat     600
acttctgttc ctgcaaacaa agtagaagaa aaaactactc aatcagaagc gtcaggcaat     660
aaacaagaag taactaagag tgaggaaaaa caggctaccct ctgatgcaaa ggcatcacag    720
cctgagtcag ctaatattgc cgattacgat agttttaaaag aagttttacg aaataatatt    780
agcaaccaag taccacacat cagtgttcaa atggagtttta aaactcaaga acaagttgac    840
gaataccaaa aaaatctcgg aagcatcatc cgggaaattg gagatacact tggaacagca    900
actgaattca atgccaaaag taacattagc acttatactc ttggtggaca aatccaacgc    960
attattgtaa aaagcgacat cacaatcacc tatactctta aaggtgacat ggtaggatta   1020
cataaagaat ataaacagtt tgtagattct tttgtcaaag aaaatattac taacaaaaat   1080
atcacaagtg atattgaaaa agctaaagta attcatgacc acttggttaa taattacact   1140
tacgcgactg aagaactggc aaccactcgt gaaactgcta gtggtatcag tatccatgct   1200
cctgaagcac tctacaaaga taaacgtggt gtttgtcaag cctttgcagt aatgtttaaa   1260
gatatggctg ctgctggctt atcagtatgg tatgtaactg gtcaagctgg aggtggaaat   1320
cacgcttgga acattgttac tattaatggc gttaaatatt atgttgatac aacatgggat   1380
aataatataa aaagcaataa atatttcctt gttggtaaaa caataatgga tgctgatcat   1440
cttttggata gtcaatacaa tgcattagct aaagatattc cagctgatcg ccatcaaggt   1500
gcataa                                                              1506
```

<210> SEQ ID NO 7
<211> LENGTH: 529
<212> TYPE: PRT
<213> ORGANISM: Group B Streptococcus

<400> SEQUENCE: 7

```
Met Lys Ile Lys Lys Ile Ile Ser Gly Phe Ala Ala Ala Leu Ile Ile
 1               5                  10                  15
Ser Ser Leu Ser Thr Ile Asn Tyr Glu Val Lys Ala Asp Asp Thr Thr
             20                  25                  30
Ser Glu Tyr His Tyr Ile Ser Lys Gln Asn Asn Glu Lys Gln Leu Ile
         35                  40                  45
Ser Tyr Ile Lys Glu Gln His Arg Leu Leu Asn Gln Phe Val Val Asp
     50                  55                  60
Asn Val Asn Ser Phe Thr Gln Leu Asn Ala Asn Pro Thr Ile Glu Gln
 65                  70                  75                  80
Leu Asn Arg Ala Ile Thr Leu Phe Lys Gln Lys Asp Glu Gln Leu Phe
```

```
                85                  90                  95
Asn Gln Val Lys Ala Gly His Leu Ser Pro Ser Asn Tyr Asn Ala Ile
            100                 105                 110
Val Asn Gln Arg Asn Val Ile Asn Gln Thr Val Gln Asn Leu Ile Asp
            115                 120                 125
Gln Asn His Asn Lys Ile Gln Thr Ser Gln Asn Lys Ala Ala Gln Leu
            130                 135                 140
Val Gly Gln Arg Asn Gln Val Val Asn Lys Ile Gln Ala Ile Leu Ala
145                 150                 155                 160
Thr Val Asn Tyr Asn Ser Val Asn Ser Ile Gln Glu Ala Glu Asn Leu
                165                 170                 175
Phe His Ser Leu Arg Asn Gln Ile Glu Pro Leu Val Ala Glu Val Asn
            180                 185                 190
Asn Tyr Lys Ala Ala Met Ala Ile Leu Gln Gln Glu Val Asp Ala Leu
            195                 200                 205
Ser Thr Ala Ala Ile Glu Thr Glu Thr Ser Lys Leu Ala Thr Leu Lys
            210                 215                 220
Val Ser Glu Asn Thr Ser Val Pro Ala Asn Lys Val Glu Glu Lys Thr
225                 230                 235                 240
Thr Gln Ser Glu Ala Ser Gly Asn Lys Gln Glu Val Thr Lys Ser Glu
                245                 250                 255
Glu Lys Gln Ala Thr Ser Asp Ala Lys Ala Ser Gln Pro Glu Ser Ala
            260                 265                 270
Asn Ile Ala Asp Tyr Asp Ser Leu Lys Glu Val Leu Arg Asn Asn Ile
            275                 280                 285
Ser Asn Gln Val Pro His Ile Ser Val Gln Met Glu Phe Lys Thr Gln
            290                 295                 300
Glu Gln Val Asp Glu Tyr Gln Lys Asn Leu Gly Ser Ile Ile Arg Glu
305                 310                 315                 320
Ile Gly Asp Thr Leu Gly Thr Ala Thr Glu Phe Asn Ala Lys Ser Asn
                325                 330                 335
Ile Ser Thr Tyr Thr Leu Gly Gly Gln Ile Gln Arg Ile Ile Val Lys
            340                 345                 350
Ser Asp Ile Thr Ile Thr Tyr Thr Leu Lys Gly Asp Met Val Gly Leu
            355                 360                 365
His Lys Glu Tyr Lys Gln Phe Val Asp Ser Phe Val Lys Glu Asn Ile
            370                 375                 380
Thr Asn Lys Asn Ile Thr Ser Asp Tyr Glu Lys Ala Lys Val Ile His
385                 390                 395                 400
Asp His Leu Val Asn Asn Tyr Thr Tyr Ala Thr Glu Glu Leu Ala Thr
                405                 410                 415
Thr Arg Glu Thr Ala Ser Gly Ile Ser Ile His Ala Pro Glu Ala Leu
            420                 425                 430
Tyr Lys Asp Lys Arg Gly Val Cys Gln Ala Phe Ala Val Met Phe Lys
            435                 440                 445
Asp Met Ala Ala Ala Gly Leu Ser Val Trp Tyr Val Thr Gly Gln Ala
            450                 455                 460
Gly Gly Gly Asn His Ala Trp Asn Ile Val Thr Ile Asn Gly Val Lys
465                 470                 475                 480
Tyr Tyr Val Asp Thr Thr Trp Asp Asn Asn Ile Lys Ser Asn Lys Tyr
                485                 490                 495
Phe Leu Val Gly Lys Thr Ile Met Asp Ala Asp His Leu Leu Asp Ser
            500                 505                 510
```

```
Gln Tyr Asn Ala Leu Ala Lys Asp Ile Pro Ala Asp Arg His Gln Gly
            515                 520                 525
Ala

<210> SEQ ID NO 8
<211> LENGTH: 501
<212> TYPE: PRT
<213> ORGANISM: Group B Streptococcus

<400> SEQUENCE: 8

Asp Asp Thr Thr Ser Glu Tyr His Tyr Ile Ser Lys Gln Asn Asn Glu
  1               5                  10                  15

Lys Gln Leu Ile Ser Tyr Ile Lys Glu Gln His Arg Leu Leu Asn Gln
             20                  25                  30

Phe Val Val Asp Asn Val Asn Ser Phe Thr Gln Leu Asn Ala Asn Pro
             35                  40                  45

Thr Ile Glu Gln Leu Asn Arg Ala Ile Thr Leu Phe Lys Gln Lys Asp
 50                  55                  60

Glu Gln Leu Phe Asn Gln Val Lys Ala Gly His Leu Ser Pro Ser Asn
 65                  70                  75                  80

Tyr Asn Ala Ile Val Asn Gln Arg Asn Val Ile Asn Gln Thr Val Gln
             85                  90                  95

Asn Leu Ile Asp Gln Asn His Asn Lys Ile Gln Thr Ser Gln Asn Lys
            100                 105                 110

Ala Ala Gln Leu Val Gly Gln Arg Asn Gln Val Val Asn Lys Ile Gln
            115                 120                 125

Ala Ile Leu Ala Thr Val Asn Tyr Asn Ser Val Asn Ser Ile Gln Glu
            130                 135                 140

Ala Glu Asn Leu Phe His Ser Leu Arg Asn Gln Ile Glu Pro Leu Val
145                 150                 155                 160

Ala Glu Val Asn Asn Tyr Lys Ala Ala Met Ala Ile Leu Gln Gln Glu
                165                 170                 175

Val Asp Ala Leu Ser Thr Ala Ala Ile Glu Thr Glu Thr Ser Lys Leu
            180                 185                 190

Ala Thr Leu Lys Val Ser Glu Asn Thr Ser Val Pro Ala Asn Lys Val
            195                 200                 205

Glu Glu Lys Thr Thr Gln Ser Glu Ala Ser Gly Asn Lys Gln Glu Val
            210                 215                 220

Thr Lys Ser Glu Glu Lys Gln Ala Thr Ser Asp Ala Lys Ala Ser Gln
225                 230                 235                 240

Pro Glu Ser Ala Asn Ile Ala Asp Tyr Asp Ser Leu Lys Glu Val Leu
                245                 250                 255

Arg Asn Asn Ile Ser Asn Gln Val Pro His Ile Ser Val Gln Met Glu
            260                 265                 270

Phe Lys Thr Gln Glu Gln Val Asp Glu Tyr Gln Lys Asn Leu Gly Ser
            275                 280                 285

Ile Ile Arg Glu Ile Gly Asp Thr Leu Gly Thr Ala Thr Glu Phe Asn
            290                 295                 300

Ala Lys Ser Asn Ile Ser Thr Tyr Thr Leu Gly Gly Gln Ile Gln Arg
305                 310                 315                 320

Ile Ile Val Lys Ser Asp Ile Thr Ile Thr Tyr Thr Leu Lys Gly Asp
                325                 330                 335

Met Val Gly Leu His Lys Glu Tyr Lys Gln Phe Val Asp Ser Phe Val
            340                 345                 350
```

```
Lys Glu Asn Ile Thr Asn Lys Asn Ile Thr Ser Asp Tyr Glu Lys Ala
            355                 360                 365

Lys Val Ile His Asp His Leu Val Asn Asn Tyr Thr Tyr Ala Thr Glu
        370                 375                 380

Glu Leu Ala Thr Thr Arg Glu Thr Ala Ser Gly Ile Ser Ile His Ala
385                 390                 395                 400

Pro Glu Ala Leu Tyr Lys Asp Lys Arg Gly Val Cys Gln Ala Phe Ala
                405                 410                 415

Val Met Phe Lys Asp Met Ala Ala Gly Leu Ser Val Trp Tyr Val
            420                 425                 430

Thr Gly Gln Ala Gly Gly Asn His Ala Trp Asn Ile Val Thr Ile
        435                 440                 445

Asn Gly Val Lys Tyr Tyr Val Asp Thr Thr Trp Asp Asn Asn Ile Lys
    450                 455                 460

Ser Asn Lys Tyr Phe Leu Val Gly Lys Thr Ile Met Asp Ala Asp His
465                 470                 475                 480

Leu Leu Asp Ser Gln Tyr Asn Ala Leu Ala Lys Asp Ile Pro Ala Asp
                485                 490                 495

Arg His Gln Gly Ala
            500
```

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide primer DMAR172

<400> SEQUENCE: 9
ctttggggaa catatgaggg gatctc                                    26

<210> SEQ ID NO 10
<211> LENGTH: 34
<212> TYPE: DNA
<213> ORGANISM: Artificial Sequence
<220> FEATURE:
<223> OTHER INFORMATION: Oligonucleotide primer DMAR173

<400> SEQUENCE: 10
ctaaaaagat ttactcgaga atttcaatat agcg                           34

<210> SEQ ID NO 11
<211> LENGTH: 31
<212> TYPE: DNA
<213> ORGANISM: Artificial Sequence
<220> FEATURE:
<223> OTHER INFORMATION: Oligonucleotide primer DMAR373

<400> SEQUENCE: 11
atgaggggat ctctcagtac taagcaatct t                              31

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide primer DMAR374

<400> SEQUENCE: 12
ttaaatttca atatagcgac gaataccgga                                30

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide primer DMAR464

<400> SEQUENCE: 13
cataggatcc ggatcaaact acatcggttc aag                33

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide primer DMAR465

<400> SEQUENCE: 14
ccgggtcgac ttaaatttca atatagcgac g                  31

<210> SEQ ID NO 15
<211> LENGTH: 46
<212> TYPE: DNA
<213> ORGANISM: Artificial Sequence
<220> FEATURE:
<223> OTHER INFORMATION: Oligonucleotide primer DMAR204

<400> SEQUENCE: 15
cacaggagaa catatgaaga ttaaaaaaat tattagtggc tttgcc   46

<210> SEQ ID NO 16
<211> LENGTH: 31
<212> TYPE: DNA
<213> ORGANISM: Artificial Sequence
<220> FEATURE:
<223> OTHER INFORMATION: Oligonucleotide primer DMAR205

<400> SEQUENCE: 16
ctttctcgag tgcaccttga tggcgatcag c                  31

<210> SEQ ID NO 17
<211> LENGTH: 41
<212> TYPE: DNA
<213> ORGANISM: Artificial Sequence
<220> FEATURE:
<223> OTHER INFORMATION: Oligonucleotide primer DMAR466

<400> SEQUENCE: 17
cataggatcc tgatgacacc accagtgagt atcactatat c       41

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide primer DMAR467

<400> SEQUENCE: 18
catagtcgac ttatgcacct tgatggcgat cag                33

<210> SEQ ID NO 19
<211> LENGTH: 28
<212> TYPE: PRT
<213> ORGANISM: Group B Streptococcus
<220> FEATURE:
<221> NAME/KEY: SIGNAL

```
-continued

<222> LOCATION: (1)...(28)

<400> SEQUENCE: 19

Met Lys Ile Lys Lys Ile Ile Ser Gly Phe Ala Ala Ala Leu Ile Ile
 1               5                  10                  15

Ser Ser Leu Ser Thr Ile Asn Tyr Glu Val Lys Ala
            20                  25

<210> SEQ ID NO 20
<211> LENGTH: 5
<212> TYPE: PRT
<213> ORGANISM: Artificial Sequence
<220> FEATURE:
<223> OTHER INFORMATION: cell wall anchoring motif
<220> FEATURE:
<221> NAME/KEY: VARIANT
<222> LOCATION: (1)...(5)
<223> OTHER INFORMATION: Xaa = Any Amino Acid

<400> SEQUENCE: 20

Leu Pro Xaa Thr Gly
 1               5

<210> SEQ ID NO 21
<211> LENGTH: 6
<212> TYPE: PRT
<213> ORGANISM: Artificial Sequence
<220> FEATURE:
<223> OTHER INFORMATION: IgA binding motif

<400> SEQUENCE: 21

Met Leu Lys Lys Ile Glu
 1               5
```